BEST AVAILABLE COPY

United States Statutory Invention Registration [19]

[11] Reg. Number: H386

Levitt

[43] Published: Dec. 1, 1987

[54] HERBICIDAL SULFONAMIDES

[75] Inventor: George Levitt, Wilmington, Del.

[73] Assignee: E. I. Du Pont de Nemours and Company, Wilmington, Del.

[21] Appl. No.: 769,686

[22] Filed: Aug. 27, 1985

[51] Int. Cl.[4] ..... A01N 43/54; C07D 239/80; C07D 491/048; C07D 491/052

[52] U.S. Cl. ..... 71/92; 544/253; 544/278

[58] Field of Search ..... 544/278, 253; 71/92

[56] References Cited

U.S. PATENT DOCUMENTS

| | | | |
|---|---|---|---|
| 4,332,611 | 6/1982 | Petersen | 544/253 |
| 4,339,267 | 7/1982 | Levitt | 544/278 |
| 4,348,219 | 9/1982 | Levitt | 544/253 |
| 4,420,325 | 12/1983 | Sauers | 544/253 |
| 4,425,153 | 1/1984 | Adams, Jr. | 544/253 |
| 4,486,589 | 12/1984 | Farnham | 544/278 |
| 4,487,626 | 12/1984 | Zimmerman | 544/278 |
| 4,515,624 | 5/1985 | Reap | 544/253 |
| 4,582,525 | 4/1986 | Chen et al. | 544/278 |

FOREIGN PATENT DOCUMENTS

| | | |
|---|---|---|
| 102924 | 3/1984 | European Pat. Off. . |
| 112803 | 7/1984 | European Pat. Off. . |
| 825042 | 7/1981 | South Africa . |
| 814874 | 1/1982 | South Africa . |
| 830441 | 7/1983 | South Africa . |
| 833779 | 11/1983 | South Africa . |
| 836449 | 3/1984 | South Africa . |
| 842722 | 10/1984 | South Africa . |

OTHER PUBLICATIONS

U.S. Patent application Ser. No. 818,395, filed 2/24/86.

*Primary Examiner*—John F. Terapane
*Assistant Examiner*—M. L. Mallon

[57] ABSTRACT

This invention relates to sulfonylureas, agriculturally suitable compositions containing them and their method-of-use as preemergent and/or postemergent herbicides or plant growth regulants.

24 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

HERBICIDAL SULFONAMIDES

BACKGROUND OF THE INVENTION

The present invention relates to sulfonylureas, agriculturally suitable compositions containing them, and their method-of-use as preemergent and/or postemergent herbicides or plant growth regulants.

U.S. Pat. No. 4,339,267 discloses, in part, herbicidal sulfonylureas of the formula

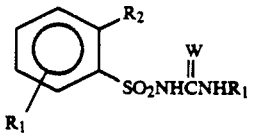

wherein $R_1$ is

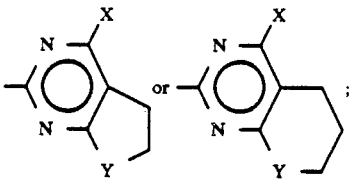

X is H, $CH_3$, $OCH_3$, Cl or $CH_2OCH_3$;

Y is O or $CH_2$; and $R_2$ is H, $CH_3$, $OCH_3$, F, Cl, Br, $NO_2$, $CF_3$, $COR_5$, $S(O)_mR_{10}$, $SO_2NR_{10}R_{11}$, $SO_2OCH_2CF_3$, $SO_2OCH_2CCl_3$ or $SO_2N(OCH_3)CH_3$.

U.S. Pat. No. 4,487,626 discloses, in part, herbicidal sulfonylureas of the formula

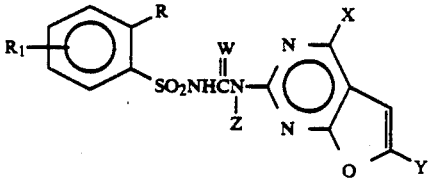

wherein

R is, among other values, H, $C_1$–$C_4$ alkyl, $C_2$–$C_4$ alkenyl, phenyl, $CH_2L$, $CH(CH_3)L$ or $BR_8$;

X is $CH_3$, $C_2H_5$, Cl, $OCH_3$, $OC_2H_5$, $N(CH_3)_2$ or $SCH_3$;

Y is H, $CH_3$ or $C_2H_5$;

L is Cl, Br, $C_1$–$C_4$ alkoxy, $C_3$–$C_4$ alkenyloxy, OH, $S(O)_mR_5$, $CO_2R_{17}$ or $SO_2N(CH_3)_2$;

B is O or $S(O)_m$; and $R_8$ is $CHF_2$, $CF_3$, $CH_2CF_3$ or $CF_2CHFG$ where G is F, Cl, Br or $CF_3$.

South African Patent Application No. 81/4874, published 1/17/82, discloses herbicidal sulfonylureas of the formula

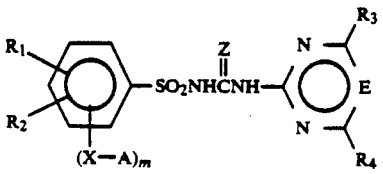

where, in part,

A is a $C_1$–$C_6$ alkyl radical substituted by halogen, $C_1$–$C_4$ alkoxy, $C_1$–$C_4$ alkylthio, etc., or a $C_2$–$C_6$ alkenyl radical which is unsubstituted or substituted by the above substituents;

X is O, S, SO or $SO_2$;

E is CH or N;

Z is O or S; etc.

South African Patent Application No. 82/5042, published 7/16/81, discloses herbicidal sulfonylureas of the formula

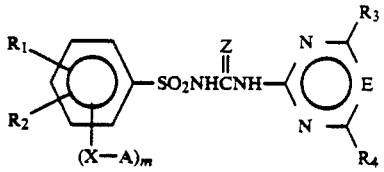

where, in part,

A is a $C_3$–$C_6$ alkynyl group;

E is CH or N;

Z is O or S;

X is O, S, SO or $SO_2$; etc.

South African Patent Application No. 83/0441, published 7/25/83, discloses herbicidal sulfonylureas of the formula

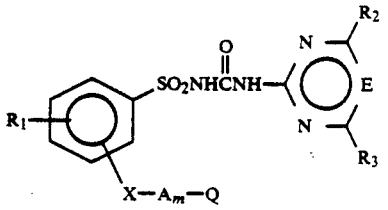

where, in part,

X is O, S, SO or $SO_2$;

m is 0 or 1;

A is $C_1$–$C_4$ alkylene or $C_2$–$C_4$ alkenylene, each unsubstituted or substituted by $C_1$–$C_4$ alkyl;

Q is, among other values, OH, CN, $NR_6R_7$, $SO_2R_8$ or $C(OR_{10})_2R_{11}$.

South African Patent Application No. 83/3779, published 11/26/83, discloses herbicidal sulfonylureas of the formula

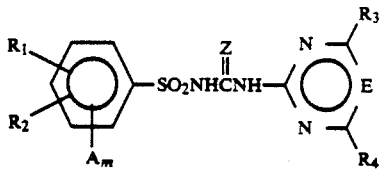

wherein

A is —C≡CR;

m is 1 or 2;

R is, among other values, H, branched or unbranched $C_1$–$C_9$ alkyl which is unsubstituted or substituted by halogen, OH, $C_1$–$C_4$ alkoxy, $C_1$–$C_4$ alkylthio, $C_1$–$C_4$ haloalkoxy or phenyl.

South African Patent Application No. 83/6449, published 3/1/84, discloses herbicidal sulfonylureas of the formula

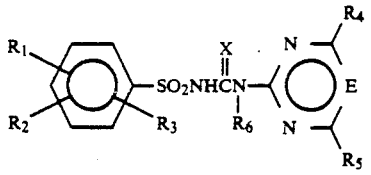

where, in part, $R_3$ is $C_2$–$C_{10}$ alkenyl which is substituted by one or more fluorine or bromine atoms or by one or more OH, CN, $NO_2$, etc.

European Publication Nos. 102,924 and 112,803 teach herbicidal benzenesulfonylureas, which can contain azide and phosphonate esters, respectively, in the position ortho to the sulfonylurea bridge.

South African Patent Application No. 84/2722, published 10/13/84, discloses herbicidal sulfonylureas of the formula

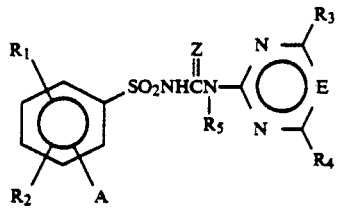

where, in part,

A is a radical of the formula $—CR_6R_7XR_8$, $—CR_9R_{10}R_{11}$ or $—CHR_7SCQR_{21}$;

$R_9$ is H, halogen, $C_1$–$C_4$ alkyl, $C_1$–$C_4$ alkoxy, $C_1$–$C_4$ alkylthio, $C_1$–$C_4$ alkylsulfinyl or $C_1$–$C_4$ alkylsulfonyl;

$R_{10}$ is H, halogen or $CH_3$;

$R_{11}$ is a radical $COR_{24}$, or a $C_1$–$C_4$ alkyl group that is mono- or polysubstituted by substituents selected from CN, $NO_2$, OH, $C_1$–$C_4$ alkoxy, $C_1$–$C_4$ alkylthio, etc.

SUMMARY OF THE INVENTION

This invention relates to compounds of Formula I, agriculturally suitable compositions containing them, and their method-of-use as preemergent and/or postemergent herbicides or plant growth regulants.

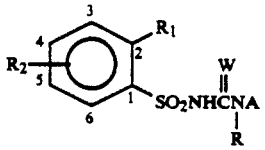

I wherein

W is O or S;

R is H or $CH_3$;

A is

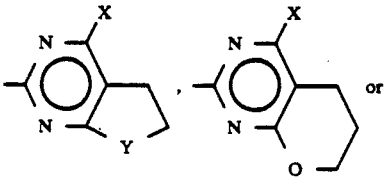

A-1 A-2

-continued

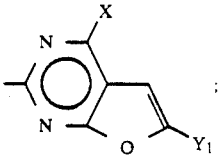

A-3

X is H, $CH_3$, $C_2H_5$, $OCH_3$, $OC_2H_5$, Cl, $OCF_2H$, $SCH_3$ or $N(CH_3)_2$;

Y is O or $CH_2$;

$Y_1$ is H, $CH_3$ or $C_2H_5$;

$R_1$ is $QR_3$, $—C{\equiv}CR_4$, $N_3$, $P(W_1)R_5R_6$, $—CR_7R_8R_9$ or $C_2$–$C_4$ alkenyl substituted with 1–3 atoms of Cl, Br or F, or with $C_1$–$C_2$ alkoxy, CN, OH, $NO_2$ or $S(O)_nR_{10}$;

$R_2$ is H, F, Cl, Br, $CF_3$, CN, $NO_2$, $C_1$–$C_2$ alkyl, $C_1$–$C_2$ alkoxy, $C_1$–$C_2$ alkylthio, $C_1$–$C_2$ haloalkyl, $C_1$–$C_2$ haloalkoxy, $C_1$–$C_2$ haloalkylthio, $C_1$–$C_2$ alkylsulfinyl, $C_1$–$C_2$ alkylsulfonyl, $CH_2OCH_3$, $CH_2SCH_3$, $C_3$ alkenyloxy or $C_3$ alkynyloxy;

Q is O, S, SO or $SO_2$;

$R_3$ is $C_1$–$C_4$ alkyl substituted with halogen, $C_1$–$C_2$ alkoxy, $C_1$–$C_2$ alkylthio, $C_1$–$C_2$ alkylsulfinyl, $C_1$–$C_2$ alkylsulfonyl, $C_1$–$C_2$ haloalkoxy, $C_1$–$C_2$ haloalkylthio, $C_1$–$C_2$ haloalkylsulfinyl, $C_1$–$C_2$ haloalkylsulfonyl, OH, CN, $NH_2$, $C_1$–$C_2$ alkylamino, di($C_1$–$C_2$)alkylamino or phenyl; or $R_3$ is $C_2$–$C_4$ alkenyl optionally substituted with the substituents mentioned above; or $R_3$ is $C_2$–$C_4$ alkynyl;

$R_4$ is H or $C_1$–$C_2$ alkyl optionally substituted with halogen, OH, $C_1$–$C_2$ alkoxy, $C_1$–$C_2$ alkylthio, $C_1$–$C_2$ haloalkoxy, CN, $C_2$–$C_3$ alkoxycarbonyl, cyclopropyl or phenyl; or $R_4$ is $C_3$–$C_6$ cycloalkyl or phenyl;

$W_1$ is O or S;

$R_5$ and $R_6$ are independently $C_1$–$C_2$ alkyl, $C_1$–$C_2$ alkoxy or $C_1$–$C_2$ alkylthio;

$R_7$ is H, $CH_3$ or halogen;

$R_8$ is H or $CH_3$;

$R_9$ is $C(O)R_{11}$ or $C_1$–$C_2$ alkyl substituted with one or more groups selected from $C(O)R_{11}$, CN, $NO_2$, $C_1$–$C_2$ haloalkoxy or $C_1$–$C_2$ haloalkylthio;

$R_{10}$ is $C_1$–$C_2$ alkyl;

$R_{11}$ is H or $C_1$–$C_2$ alkyl; and n is 0, 1 or 2;

and their agriculturally suitable salts; provided that (1) when A is A-3, then $R_3$ is other than $CF_2H$, $CF_3$, $CH_2CF_3$, $CF_2CHF_2$, $CF_2CHFCl$, $CH_2CHFBr$ or $CF_2CHFCF_3$;

(2) when A is A-1 or A-2 and Q is S, SO or $SO_2$, then $R_3$ is other than unsubstituted $C_3$–$C_4$ alkenyl;

(3) when $R_3$ is substituted with OH or $NH_2$, said substituents must be separated from Q by at least two carbon atoms; and (4) when A is A-1 or A-2, then $R_1$ is other than $CH{=}CBr_2$, $CH{=}CHOCH_3$, $CH{=}CHOC_2H_5$, $CH{=}CF_2$ or $C_2$–$C_3$ alkenyl substituted with 1–3 chlorine atoms.

In the above definitions, the term "alkyl", used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy or ethoxy.

Alkenyl denotes straight chain or branched alkenes, e.g. 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl", said alkyl may contain as few as one halogen atom, or may be fully substituted with halogen atoms which may be the same or different. Examples of haloalkyl include $CH_2CH_2F$, $CF_2CF_3$ and $CH_2CHBrCl$.

The total number of carbon atoms in a substituent group is indicated by the $C_i$–$C_j$ prefix where i and j are numbers from 1 to 4. For example, $C_1$–$C_2$ alkylsulfonyl would designate methylsulfonyl and ethylsulfonyl; $C_1$–$C_2$ alkylamino would designate $NHCH_3$ and $NHC_2H_5$; and $C_2$–$C_3$ alkoxycarbonyl denotes methoxycarbonyl and ethoxycarbonyl.

Preferred for reasons of increased ease of synthesis and/or greater herbicidal efficacy are:

(1) Compounds of Formula I where
W is O; and
R is H;

(2) Compounds of Preferred 1 where
$R_1$ is $OR_3$, $SR_3$, $SO_2R_3$, —C≡$CR_4$, $N_3$, $P(O)R_5R_6$, —$CH_2R_9$ or $C_2$–$C_4$ alkenyl substituted with 1–3 atoms of Cl, Br or F, or with CN, OH, $NO_2$, $SCH_3$, $SC_2H_5$, $SO_2CH_3$, $SO_2C_2H_5$, $OCH_3$ or $OC_2H_5$;
$R_2$ is H, Cl, Br, F, $CH_3$, $C_2H_5$, $OCH_3$, $OC_2H_5$, $SCH_3$, CN, $CF_3$, $OCF_2H$, $SCF_2H$, $CH_2OCH_3$ or $CH_2SCH_3$, and $R_2$ must be H when in the 4-position;
$R_3$ is $C_1$–$C_3$ alkyl substituted with F, Cl, Br, $OCH_3$, $OC_2H_5$, $SCH_3$, $SC_2H_5$, $SO_2CH_3$, $SO_2C_2H_5$, $OCF_2H$, $OCH_2CF_3$, $SCF_2H$, $SO_2CF_3$, OH, CN, $NH_2$, $NHCH_3$, $N(CH_3)_2$ or phenyl; or $R_3$ is $C_2$–$C_4$ alkenyl optionally substituted with 1–3 atoms of Cl, F or Br; or $R_3$ is $C_3$–$C_4$ alkynyl;
$R_4$ is H or $C_1$–$C_2$ alkyl optionally substituted with halogen, OH, CN, $OCH_3$, $SCH_3$, $OCF_2H$, $OCH_2CF_3$, cyclopropyl, $CO_2CH_3$ or phenyl;
$R_5$ and $R_6$ are independently $C_1$–$C_2$ alkyl or $C_1$–$C_2$ alkoxy; and
$R_9$ is $C(O)CH_3$, $CH_2CH_2CN$, $CH_2CN$, $CH_2C(O)CH_3$, $CH_2CH_2C(O)CH_3$, $CH_2OCF_2H$ or $CH_2SCF_2H$;

(3) Compounds of Preferred 2 where
X is $CH_3$, $OCH_3$, $OC_2H_5$ or $OCF_2H$; and
$Y_1$ is H or $CH_3$;

(4) Compounds of Preferred 3 where
$R_1$ is $OR_3$, $SR_3$, $SO_2R_3$, —C≡CH, —C≡$CCH_3$, $N_3$, $P(O)(OCH_3)_2$, $P(O)(CH_3)_2$ or $C_2$–$C_3$ alkenyl substituted with 1–3 atoms of Cl or F or with 1 Br;
$R_2$ is H, Cl, $CH_3$ or $OCH_3$; and
$R_3$ is $C_1$–$C_2$ alkyl substituted with F, Cl, Br, $OCH_3$ or $OC_2H_5$; or $R_3$ is $C_2$–$C_3$ alkenyl substituted with 1–3 atoms of F, Cl or Br;

(5) Compounds of Preferred 4 where A is A-1;

(6) Compounds of Preferred 4 where A is A-2;

(7) Compounds of Preferred 4 where A is A-3.

Specifically preferred for reasons of greatest ease of synthesis and/or greatest herbicidal efficacy are:

2-(difluoromethoxy)-N-[(5,6-dihydro-4-methylfuro[2,3-d]pyrimidin-2-yl)aminocarbonyl]-6-methylbenzenesulfonamide, m.p. 213°–215° C.;

2-(1,2-dichloroethenyloxy)-N-[(5,6-dihydro-4-methylfuro[2,3-d]pyrimidin-2-yl)aminocarbonyl]benzenesulfonamide, m.p. 208°–210° C.; and 2-difluoromethylthio-N-[(5,6-dihydro-4-methylfuro[2,3-d]pyrimidin-2-yl)aminocarbonyl]benzenesulfonamide, m.p. 184°–189° C.

DETAILED DESCRIPTION OF THE INVENTION

Synthesis

The compounds of Formula I can be prepared by methods described or referred to in U.S. Pat. Nos. 4,169,719; 4,127,405; 4,339,267 and 4,394,506.

Compounds of Formula I can also be prepared by one or more of the methods shown in Equations 1–7.

As shown in Equation 1, compounds of Formula I can be prepared by treating sulfonamides of Formula II with phenyl esters of N-heterocyclic carbamic acids of Formula III in the presence of a strong organic base such as 1,8-diazabicyclo[5.4.0]undec-7-ene (DBU).

Equation 1

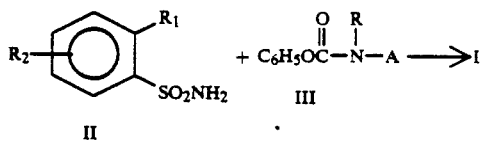

wherein R, $R_1$, $R_2$ and A are as previously defined.

The reaction of Equation 1 is generally carried out in the range of 20° to 50° C. in an inert solvent such as dioxane or acetonitrile, analogous to methods taught in EP-A No. 44,807. The required carbamates can be prepared from the corresponding amines, IIIa, and diphenyl carbonate or phenylchloroformate and a base such as sodium hydride as shown in Equation 2.

Equation 2

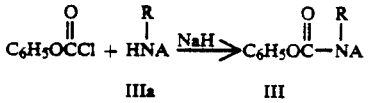

Compounds of Formula I may also be prepared as shown in Equation 3 by treating sulfonamides of Formula II with the methyl ester of an N-heterocyclic carbamic acid of Formula IIIb in presence of an equimolar quantity of trimethylaluminum.

Equation 3

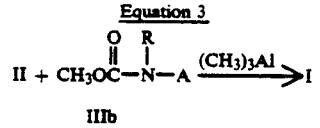

The reaction of Equation 3 is best carried out at temperatures between 25° and 83° C. in a solvent such as methylene chloride or 1,2-dichloroethane for 12 to 95 hours under an inert atmosphere, as taught in EP-A No. 84,244. The methyl carbamates, IIIb, can be conveniently synthesized by treatment of the corresponding heterocyclic amines of Formula IIIa with dimethyl carbonate or methyl chloroformate in the presence of a base such as sodium hydride.

Alternatively, compounds of Formula I can be prepared by the reaction of a sulfonylcarbamate of Formula IV with an aminoheterocycle of Formula IIIa as shown in Equation 4.

Equation 4

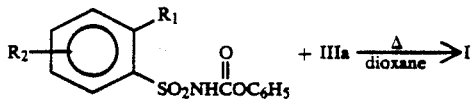

IV

The reaction is carried out at 50° to 100° C. in a solvent such as dioxane for 0.5 to 24 hours as taught in EP-A No. 44,807. The required carbamates of Formula IV are prepared by the reaction of the corresponding sulfonamides of Formula II with diphenylcarbonate or phenylchloroformate in the presence of a base such as sodium hydride.

Sulfonamides of Formula II used in the preparation of compounds of Formula I are useful intermediates. They can be prepared by a variety of methods known in the art. For example, contacting an appropriately substituted sulfonyl chloride IIa with ammonium hydroxide or ammonia in an inert solvent such as ether or tetrahydrofuran affords sulfonamides II as shown by Equation 5a and 5b.

Equation 5

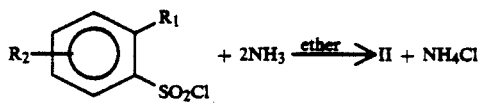

IIa (a)

$$IIa + 2NH_4OH \longrightarrow II + NH_4Cl \quad (b)$$

The reaction of sulfonyl chloride, IIa, with ammonia is best carried out at −33° to 50° C. for 0.1 to 24 hours. After removal of the ammonium chloride by-product by filtration or extraction with water, the desired product can be isolated by the evaporation of the organic solvent.

Ammonium hydroxide can be used in place of ammonia as in Equation 5b. This reaction is widely reported in the literature, c.f., *Methoden Der Organischen Chemie* (Houben-Weyl), vol. 9, Ch. 19, edited by F. Muth, Stuttgart, 1955.

Alternatively, sulfonamides of Formula II can be prepared by the reaction of a lithium salt of an appropriately substituted sulfinic acid, IIb, with chloramine as shown in Equation 6.

Equation 6

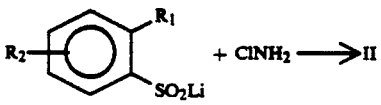

IIb

This reaction can be carried out using the conditions referred to in the preceding reference.

Lithium salts of Formula IIb can also be converted to the sulfonamides of Formula IIa by the procedures taught in U.S. Pat. No. 4,441,910.

Sulfonyl chlorides of Formula IIa can be prepared by the reaction of lithium salts of Formula IIc with sulfuryl chloride at −50° to −20° C. in an inert solvent such as tetrahydrofuran or ether as shown in Equation 7.

Equation 7

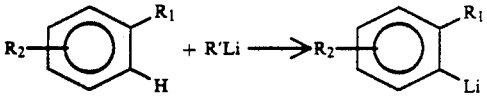

IIc (a)

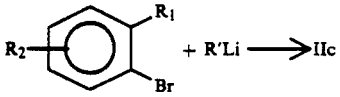

(b)

$$IIc + SO_2Cl_2 \longrightarrow IIa \quad (c)$$

In Equation 7, R′ is a group such as butyl, phenyl, diisopropylamido or similar moiety commonly employed as lithiation agents. These agents and their method of use are described in N. S. Narasimhan and R. S. Mali, *Synthesis*, 957–86 (1983) or in *The Chemistry of Organolithium Compounds*, Wakefield, Pergamon Press, Oxford, 1974 or also H. W. Gschwend and H. R. Rodriguez, *Org. React.* 26, 1 (1978).

The sulfonyl chlorides, IIa, can be isolated by extracting the inorganic by-products with water followed by drying the organic layer over a drying agent such as magnesium sulfate, filtering the dried solution and evaporation of the solvent.

Lithium salts of formula IIb can be prepared by contacting sulfur dioxide with the lithiated intermediate IIc using procedures described in the above references.

Sulfonamides of Formula II can be synthesized by methods described in U.S. Pat. No. 4,452,628 where $R_1$ is haloalkoxy; U.S. Pat. No. 4,368,069 and South African Patent Application No. 83/6449 where $R_1$ is substituted alkenyl. (EP-A) No. 102,924 described methods of synthesis for sulfonamides where $R_1$ is azido; South African Patent Application No. 83/3779 discloses methods for the synthesis of sulfonamides where $R_1$ is alkynyl and (EP-A) No. 112,803 describes the synthesis of sulfonamides of Formula II where $R_1$ is dialkoxyphosphonyloxy.

The synthesis of heterocyclic amine derivatives such as those depicted by Formula IIIa where A is A-1, A-2 or A-3 is described in the following references:

W. Braker, J. T. Sheehan, E. R. Spitmiller and W. A. Lott, *J. Am. Chem. Soc.*, 69, 3072 (1947);

P. C. Mitter and A. Bhattacharya, *Quart. J. Indian Chem. Soc.*, 4, 152 (1927);

A. Shrage and G. H. Hitchings, *J. Org. Chem.*, 16, 1153 (1951);

W. T. Caldwell, E. C. Kornfeld and C. K. Donnell, *J. Am. Chem. Soc.*, 63, 2188 (1941); and J. D. Fissekis, A. Myles and G. B. Brown, *J. Org. Chem.*, 29, 2670 (1964).

Agriculturally suitable salts of compounds of Formula I are also useful herbicides and can be prepared in a number of ways known in the art. For example, metal salts can be made by contacting compounds of Formula I with a solution of an alkali or alkaline earth metal salt having a sufficiently basic anion (e.g., hydroxide, alkoxide or carbonate). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Unless otherwise indicated, temperatures are given in degrees centigrade.

EXAMPLE 1

1,2-Dichloro-1-(2-nitrophenoxy)ethene

To 139.11 g of 2-nitrophenol in 500 ml of dimethylformamide was added 276.42 g of anhydrous potassium carbonate. The mixture was warmed ot 60° to form a red suspension and 100 ml of 1,1,2-trichloroethene was added dropwise. After stirring at 85° for 16 hours the mixture was cooled to room temperature, stirred for 4 hours at room temperature and then poured into 3 l of ice and water. The aqueous mixture was extracted five times with 500 ml portions of methylene chloride and the methylene chloride extracts were then washed with three portions of 500 ml 10% hydrochloric acid followed by three washes with 600 ml of water and one wash with 600 ml of saturated aqueous sodium chloride. After drying the organic phase over magnesium sulfate and evaporation of the solvent, 218.5 g of a yellow solid was obtained.

NMR ($CDCl_3$): 7.99 (d, 1H, Armo.); 7.63 (t, 1H, Arom.); 7.31 (m, 2H, Arom.); and 6.08 (s, 1H, =CClH).

EXAMPLE 2

1-(2-Aminophenoxy)-1,2-dichloroethene

Two hundred and eighteen grams of 1,2-dichloro-1-(2-nitrophenoxy)ethene in ethyl acetate with 2.2 g of 10% palladium-on-charcoal was treated with 60 pounds per square inch gauge of hydrogen at 60° until there was no further uptake of hydrogen. The reaction mixture was filtered through Celite® and concentrated in vacuo to yield a brown oil. This oil was taken up in 20% ethyl acetate/hexane and passed through a column of Florisil® two times to yield 169.5 g of oil after evaporation of the solvent.

NMR ($CDCl_3$): 6.95 (d, 2H, Arom.); 6.8 (d, 2H, Arom.); 5.85 (s, 1H, =CHCl); and 3.75 (broad s, 2H, $NH_2$).

EXAMPLE 3

2-(1,2-Dichloroethen-1-yloxy)benzenesulfonamide

Twenty four grams of 1-(2-aminophenoxy)-1,2-dichloroethene was dissolved in a mixture of 25 ml acetic acid, 25 ml of 12N hydrochloric acid and 50 ml of water. The grown mixture was cooled to 0° and a solution of 8.28 g of sodium nitrite in 15 ml of water was added dropwise. The resulting brown suspension was stirred at below 5° for one-half hour and then added to a stirred suspension of 3 g copper sulfate, 90 ml of 12N hydrochloric acid and 62 ml of 40% sodium bisulfite. The resultant mixture was allowed to warm to room temperature and stirred for sixteen hours. It was then extracted with methylene chloride, the combined organic phases washed with water and saturated aqueous sodium chloride, dried over magnesium sulfate and added dropwise to 100 ml of methylene chloride containing 12.5 ml of liquified ammonia at −78°. This mixture was allowed to stir for two days at room temperature, then cooled to 0° and acidified with 10% hydrochloric acid. After separating the resultant two phases, the methylene chloride phase was washed with water and saturated sodium chloride followed by drying over magnesium sulfate and evaporation of the solvent to give 18.79 g of a solid melting at 145°-148°.

NMR ($CDCl_3$): 8.00 (d, 1H, Arom.); 7.60 (t, 1H, Arom.); 7.30 (t, 1H, Arom.); 7.10 (d, 1H, Arom.); 6.15 (s, 1H, =CClH); and 5.10 (bs, 2H, $NH_2$).

EXAMPLE 4

N-(n-Butylaminocarbonyl)-2-(1,2-dichloroethen-1-yloxy)benzenesulfonamide 2-(1,2-Dichloroethen-1-yloxy)benzenesulfonamide (13.4 g), 12.4 g of n-butyl isocyanate and 15.2 g of anhydrous potassium carbonate were combined in 200 ml of dry tetrahydrofuran and heated to reflux for three hours. The mixture was then cooled to room temperature, filtered and the solvent removed by evaporation. The residue and precipitate were recombined and dissolved in 600 ml of water and the mixture acidified with 10% hydrochloric acid. The resultant precipitate was removed by filtration, washed with water, air dried and then washed with hexane. After drying in vacuo at 80° overnight, 13.65 g of solid product melting at 122°-125° was obtained.

NMR ($CDCl_3$): 8.01 (d, 1H, Arom.); 7.65 (t, 1H, Arom.); 7.31 (t, 1H, Arom.); 7.12 (d, 1H, Arom.); 6.48 (broad s, 1H, NH); 6.14 (s, 1H, CH); 3.21 (q, 2H, $Ch_2$); 1.41 (m, 2H, $Ch_2$); 1.27 (m, 2H, $Ch_2$); and 0.87 (t, 3H, $Ch_3$).

EXAMPLE 5

2-(1,2-Dichloroethen-1-yloxy)benzenesulfonyl isocyanate

N-(n-Butylaminocarbonyl)-2-(1,2-dichloroethen-1-yloxy)benzenesulfonamide (11.03 g), 2.97 g of n-butyl isocyanate and 0.3 g of 1,4-diazabicyclo[2.2.2]octane (DABCO®) in xylene was heated to 135° and 2.2 ml of liquified phosgene was added portionwise while maintaining the temperature at 135°. The mixture was heated for 1.5 hours after all of the phosgene had been added, filtered and the xylene removed in vacuo to yield 10.8 g of an amber oil. The peak at 2220 $cm^{-1}$ by infrared absorption spectroscopy confirmed the presence of the isocyanate function. This oil was diluted to 120 ml in methylene chloride.

EXAMPLE 6

2-(1,2-Dichloroethen-1yloxy)-N-[(5,6-dihydro-4-methylfuro[2,3-d]pyrimidin-2-yl)aminocarbonyl]-benzenesulfonamide To 300 mg of 2-amino-5,6-dihydro-4-methylfuro[2,3-d]pyrimidine in 25 ml of methylene chloride was added 20 ml of 2-(1,2-dichloroethen-1-yloxy)benzenesulfonyl isocyanate in methylene chloride from the previous example. After heating to reflux, the mixture was stirred overnight at room temfperature. Removal of the solvent in vacuo yielded an amber oil. Trituration of this oil with 1-chlorobutane gave a tan solid. After filtration and washing with ethyl ether, a yield of 0.8 g of a tan solid melting at 208°–210° was obtained.

NMR ($CDCl_3$): 13.72 (broad s, 1H, NH); 9.18 (broad s, 1H, NH); 8.16 (d, 1H, Arom.); 7.63 (t, 1H, Arom.); 7.33 (t, 1H, Arom.); 7.07 (d, 1H, Arom.); 6.05 (s, 1H, CH); 4.73 (t, 2H, $CH_2$); 3.21 (t, 2H, $CH_2$); and 2.41 (t, 3H, $CH_3$).

An infrared absorption peak at 1690 $cm^{-1}$ was consistent for the desired urea carbonyl.

EXAMPLE 7

2-Difluoromethoxy-6-methylbenzenesulfonyl isocyanate

A mixture of 11.2 g of 2-difluoromethoxy-6-methylbenzenesulfonamide, 3 g of n-butyl isocyanate and several crystals (ca. 0.1 g) of DABCO® in 50 ml of mixed xylenes was heated under a dry ice reflux condenser to 135°. Phosgene was then passed into the flask until the temperature dropped to 120° whereupon the phosgene addition was halted. The addition was resumed when the temperature rose to 130° and once again halted when the reflux temperature had fallen to 120°. When the reflux remained at 120° without further addition of phosgene, the reaction was considered complete. The mixture was allowed to stand overnight at room temperature, filtered and the xylene distilled in vacuo. The solidified residue was triturated with 50 ml of 1-chlorobutane, filtered and the 1-chlorobutane distilled in vacuo to yield 8.3 g of the sulfonyl isocyanate whch showed a peak at 2240 $cm^{-1}$ by infrared absorption spectroscopy. This material resolidified.

EXAMPLE 8

2-(Difluoromethoxy)-N-[(5,6-dihydro-4-methylfuro-[2,3-d]pyrimidin-2-yl)aminocarbonyl]-6-methylbenzenesulfonamide A mixture of 25 ml of methylene chloride, 0.8 g of 2-amino-5,6-dihydro-4-methylfuro[2,3-d]pyrimidine, a small crystal of DABCO® (Ca<0.1 g) and 1.5 g of 2-difluoromethoxy-6-methylbenzenesulfonyl isocylanate was heated to reflux for one hour, cooled and filtered to yield 1.7 g of solid, m.p. 213°–215°. It showed peaks at 1690 and 1640 $cm^{-1}$ by infrared absorption spectroscopy, consistent for the desired product.

Using the procedures described above in Equations 1–7 and Examples 1–8, one skilled in the art can prepare the following compounds.

TABLE I

General Structure

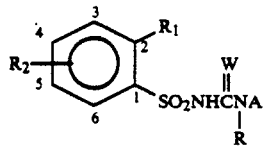

A = A-1

| $R_1$ | $R_2$ | R | W | X | Y | m.p. (°C.) |
|---|---|---|---|---|---|---|
| $OCF_2H$ | H | H | O | H | O | |
| $OCF_2H$ | H | H | O | $CH_3$ | O | |
| $OCF_2H$ | H | H | O | $C_2H_5$ | O | |
| $OCF_2H$ | H | H | O | $OCH_3$ | O | |
| $OCF_2H$ | H | H | O | $OC_2H_5$ | O | |
| $OCF_2H$ | H | H | O | Cl | O | |
| $OCF_2H$ | H | H | O | $OCF_2H$ | O | |
| $OCF_2H$ | H | H | O | $SCH_3$ | O | |
| $OCF_2H$ | H | H | O | $N(CH_3)_2$ | O | |
| $OCF_2H$ | H | H | O | H | $CH_2$ | |
| $OCF_2H$ | H | H | O | $CH_3$ | $CH_2$ | |
| $OCF_2H$ | H | H | O | $C_2H_5$ | $CH_2$ | |
| $OCF_2H$ | H | H | O | $OCH_3$ | $CH_2$ | |
| $OCF_2H$ | H | H | O | $OC_2H_5$ | $CH_2$ | |
| $OCF_2H$ | H | H | O | Cl | $CH_2$ | |
| $OCF_2H$ | H | H | O | $OCF_2H$ | $CH_2$ | |
| $OCF_2H$ | H | H | O | $SCH_3$ | $CH_2$ | |
| $OCF_2H$ | H | H | O | $N(CH_3)_2$ | $CH_2$ | |
| $OCF_2H$ | 6-$CH_3$ | H | O | $OCH_3$ | $CH_2$ | |
| $OCF_2H$ | 6-$CH_3$ | H | O | $OCH_3$ | O | |
| $OCF_2H$ | 6-$CH_3$ | H | O | $OCF_2H$ | O | |
| $O(CH_2)_2Cl$ | H | H | O | $CH_3$ | O | |
| $O(CH_2)_2Cl$ | H | H | O | $OCH_3$ | O | |
| $O(CH_2)_2Cl$ | H | H | O | $OCH_3$ | $CH_2$ | |
| $OCCl{=}CHCl$ | H | H | O | $OCH_3$ | $CH_2$ | |
| $OCCl{=}CHCl$ | H | H | O | $OCH_3$ | O | |
| $OCH_2CCl{=}CHCl$ | H | H | O | $OCH_3$ | O | |
| $OCH_2CCl{=}CHCl$ | H | H | O | $CH_3$ | O | |
| $OCF_2CF_2H$ | H | H | O | $OCH_3$ | O | |
| $OCF_2CF_2H$ | H | H | O | $CH_3$ | O | |

TABLE I-continued

General Structure

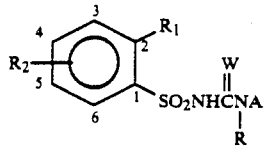

A = A-1

| $R_1$ | $R_2$ | R | W | X | Y | m.p. (°C.) |
|---|---|---|---|---|---|---|
| $OCF_2CF_2H$ | H | H | O | $OCH_3$ | $CH_2$ | |
| $O(CH_2)_2Cl$ | H | H | O | $OCH_3$ | O | |
| $O(CH_2)_2Cl$ | H | H | O | $CH_3$ | O | |
| $OCH_2CCl_3$ | H | H | O | $OCH_3$ | O | |
| $OCH_2CCl_3$ | H | H | O | $CH_3$ | O | |
| $O(CH_2)_2OCH_3$ | H | H | O | $OCH_3$ | O | |
| $O(CH_2)_2OCH_3$ | H | H | O | $CH_3$ | O | |
| $O(CH_2)_3OCH_3$ | H | H | O | $OCH_3$ | O | |
| $O(CH_2)_3OCH_3$ | H | H | O | $CH_3$ | O | |
| $O(CH_2)_2OC_2H_5$ | H | H | O | $OCH_3$ | O | |
| $O(CH_2)_2OC_2H_5$ | H | H | O | $CH_3$ | O | |
| $O(CH_2)_2SCH_3$ | H | H | O | $OCH_3$ | O | |
| $O(CH_2)_2SCH_3$ | H | H | O | $CH_3$ | O | |
| $O(CH_2)_2SC_2H_5$ | H | H | O | $OCH_3$ | O | |
| $O(CH_2)_2SC_2H_5$ | H | H | O | $CH_3$ | O | |
| $O(CH_2)_2SOCH_3$ | H | H | O | $OCH_3$ | O | |
| $O(CH_2)_2SOCH_3$ | H | H | O | $CH_3$ | O | |
| $O(CH_2)_2SO_2C_2H_5$ | H | H | O | $OCH_3$ | O | |
| $O(CH_2)_2SO_2C_2H_5$ | H | H | O | $CH_3$ | O | |
| $O(CH_2)_2O(CH_2)_2Cl$ | H | H | O | $OCH_3$ | O | |
| $O(CH_2)_2O(CH_2)_2Cl$ | H | H | O | $CH_3$ | O | |
| $O(CH_2)_2OCH_2CF_3$ | H | H | O | $OCH_3$ | O | |
| $O(CH_2)_2OCH_2CF_3$ | H | H | O | $CH_3$ | O | |
| $O(CH_2)_3O(CH_2)_2F$ | H | H | O | $OCH_3$ | O | |
| $O(CH_2)_3O(CH_2)_2F$ | H | H | O | $CH_3$ | O | |
| $O(CH_2)_2OCH_2CHF_2$ | H | H | O | $OCH_3$ | O | |
| $O(CH_2)_2OCH_2CHF_2$ | H | H | O | $CH_3$ | O | |
| $O(CH_2)_2S(CH_2)_2Cl$ | H | H | O | $OCH_3$ | O | |
| $O(CH_2)_2S(CH_2)_2Cl$ | H | H | O | $CH_3$ | O | |
| $O(CH_2)_2SO(CH_2)_2Cl$ | H | H | O | $OCH_3$ | O | |
| $O(CH_2)_2SO(CH_2)_2Cl$ | H | H | O | $CH_3$ | O | |
| $O(CH_2)SO_2(CH_2)_2Cl$ | H | H | O | $OCH_3$ | O | |
| $O(CH_2)SO_2(CH_2)_2Cl$ | H | H | O | $CH_3$ | O | |
| $O(CH_2)_2OH$ | H | H | O | $OCH_3$ | O | |
| $O(CH_2)_2OH$ | H | H | O | $CH_3$ | O | |
| $OCH_2CN$ | H | H | O | $OCH_3$ | O | |
| $OCH_2CN$ | H | H | O | $CH_3$ | O | |
| $OCH(CH_3)CN$ | H | H | O | $OCH_3$ | O | |
| $OCH(CH_3)CN$ | H | H | O | $CH_3$ | O | |
| $O(CH_2)_2NH_2$ | H | H | O | $OCH_3$ | O | |
| $O(CH_2)_2NH_2$ | H | H | O | $CH_3$ | O | |
| $O(CH_2)_3N(CH_3)_2$ | H | H | O | $OCH_3$ | O | |
| $O(CH_2)_3N(CH_3)_2$ | H | H | O | $CH_3$ | O | |
| $O(CH_2)_2NHCH_3$ | H | H | O | $OCH_3$ | O | |
| $O(CH_2)_2NHCH_3$ | H | H | O | $CH_3$ | O | |
| $OCH_2C_6H_5$ | H | H | O | $OCH_3$ | O | |
| $OCH_2C_6H_5$ | H | H | O | $CH_3$ | O | |
| $OCH_2CCl{=}CHCl$ | H | H | O | $OCH_3$ | O | |
| $OCH_2CCl{=}CHCl$ | H | H | O | $CH_3$ | O | |
| $OCH_2CH{=}CHCl$ | H | H | O | $OCH_3$ | O | |
| $OCH_2CH{=}CHCl$ | H | H | O | $CH_3$ | O | |
| $OCH_2CH{=}CHBr$ | H | H | O | $OCH_3$ | O | |
| $OCH_2CH{=}CHBr$ | H | H | O | $CH_3$ | O | |
| $OCH_2C{=}CH{-}CH_2Cl$ | H | H | O | $OCH_3$ | O | |
| $OCH_2C{=}CH{-}CH_2Cl$ | H | H | O | $CH_3$ | O | |
| $OCH_2CH{=}CHCH_2SCH_3$ | H | H | O | $OCH_3$ | O | |
| $OCH_2CH{=}CHCH_2SCH_3$ | H | H | O | $CH_3$ | O | |
| $OCH_2CH{=}CHS(O)CH_3$ | H | H | O | $OCH_3$ | O | |
| $OCH_2CH{=}CHS(O)CH_3$ | H | H | O | $CH_3$ | O | |
| $OCH_2CH{=}CHCH_2SO_2CH_3$ | H | H | O | $OCH_3$ | O | |
| $OCH_2CH{=}CHCH_2SO_2CH_3$ | H | H | O | $CH_3$ | O | |
| $OCH_2CH{=}CHCH_2OH$ | H | H | O | $OCH_3$ | O | |
| $OCH_2CH{=}CHCH_2OH$ | H | H | O | $CH_3$ | O | |
| $OCH{=}CH{-}CN$ | H | H | O | $OCH_3$ | O | |
| $OCH{=}CH{-}CN$ | H | H | O | $CH_3$ | O | |
| $OCH{=}CHCH_2NH_2$ | H | H | O | $OCH_3$ | O | |
| $OCH{=}CHCH_2NH_2$ | H | H | O | $CH_3$ | O | |
| $OCH_2CH{=}CHCH_2N(CH_3)_2$ | H | H | O | $OCH_3$ | O | |
| $OCH_2CH{=}CHCH_2N(CH_3)_2$ | H | H | O | $CH_3$ | O | |
| $OCH_2CH{=}CHC_6H_5$ | H | H | O | $OCH_3$ | O | |

TABLE I-continued

General Structure

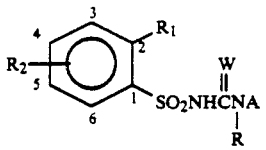

A = A-1

| $R_1$ | $R_2$ | R | W | X | Y | m.p. (°C.) |
|---|---|---|---|---|---|---|
| $OCH_2CH{=}CHC_6H_5$ | H | H | O | $CH_3$ | O | |
| $OCH_2C{\equiv}C{-}CH_3$ | H | H | O | $OCH_3$ | O | |
| $OCH_2C{\equiv}C{-}CH_3$ | H | H | O | $CH_3$ | O | |
| $OCH_2C{\equiv}CH$ | H | H | O | $OCH_3$ | O | |
| $OCH_2C{\equiv}CH$ | H | H | O | $CH_3$ | O | |
| $C{\equiv}CH$ | H | H | O | $OCH_3$ | O | |
| $C{\equiv}CH$ | H | H | O | $CH_3$ | O | |
| $C{\equiv}CCH_3$ | H | H | O | $OCH_3$ | O | |
| $C{\equiv}CCH_3$ | H | H | O | $CH_3$ | O | |
| $C{\equiv}CC_2H_5$ | H | H | O | $OCH_3$ | O | |
| $C{\equiv}CC_2H_5$ | H | H | O | $CH_3$ | O | |
| $C{\equiv}CCH_2Cl$ | H | H | O | $OCH_3$ | O | |
| $C{\equiv}CCH_2Cl$ | H | H | O | $CH_3$ | O | |
| $C{\equiv}CCHCl_2$ | H | H | O | $OCH_3$ | O | |
| $C{\equiv}CCHCl_2$ | H | H | O | $CH_3$ | O | |
| $C{\equiv}C{-}CH_2{-}CCl_3$ | H | H | O | $OCH_3$ | O | |
| $C{\equiv}C{-}CH_2{-}CCl_3$ | H | H | O | $CH_3$ | O | |
| $C{\equiv}CCH_2OH$ | H | H | O | $OCH_3$ | O | |
| $C{\equiv}CCH_2OH$ | H | H | O | $CH_3$ | O | |
| $C{\equiv}CCH_2OCH_3$ | H | H | O | $OCH_3$ | O | |
| $C{\equiv}CCH_2OCH_3$ | H | H | O | $CH_3$ | O | |
| $C{\equiv}CCH_2OC_2H_5$ | H | H | O | $OCH_3$ | O | |
| $C{\equiv}CCH_2OC_2H_5$ | H | H | O | $CH_3$ | O | |
| $C{\equiv}CCH_2SC_2H_5$ | H | H | O | $OCH_3$ | O | |
| $C{\equiv}CCH_2SC_2H_5$ | H | H | O | $CH_3$ | O | |
| $C{\equiv}CCH_2OCH_2CCl_3$ | H | H | O | $OCH_3$ | O | |
| $C{\equiv}CCH_2OCH_2CCl_3$ | H | H | O | $CH_3$ | O | |
| $C{\equiv}CCH_2CN$ | H | H | O | $OCH_3$ | O | |
| $C{\equiv}CCH_2CN$ | H | H | O | $CH_3$ | O | |
| $C{\equiv}CCH_2CO_2CH_3$ | H | H | O | $OCH_3$ | O | |
| $C{\equiv}CCH_2CO_2CH_3$ | H | H | O | $CH_3$ | O | |
| $C{\equiv}CCH(CH_3)CO_2C_2H_5$ | H | H | O | $OCH_3$ | O | |
| $C{\equiv}CCH(CH_3)CO_2C_2H_5$ | H | H | O | $CH_3$ | O | |
| $C{\equiv}CCH_2$—cyclopropyl | H | H | O | $OCH_3$ | O | |
| $C{\equiv}CCH_2$—cyclopropyl | H | H | O | $CH_3$ | O | |
| $C{\equiv}CCH_2C_6H_5$ | H | H | O | $OCH_3$ | O | |
| $C{\equiv}CCH_2C_6H_5$ | H | H | O | $CH_3$ | O | |
| $C{\equiv}C$—cyclopentyl | H | H | O | $OCH_3$ | O | |
| $C{\equiv}C$—cyclopentyl | H | H | O | $CH_3$ | O | |
| $C{\equiv}C$—cyclohexyl | H | H | O | $OCH_3$ | O | |
| $C{\equiv}C$—cyclohexyl | H | H | O | $CH_3$ | O | |
| $C{\equiv}CC_6H_5$ | H | H | O | $OCH_3$ | O | |
| $C{\equiv}CC_6H_5$ | H | H | O | $CH_3$ | O | |
| $N_3$ | H | H | O | $OCH_3$ | O | |
| $N_3$ | H | H | O | $CH_3$ | O | |
| $P(O)(CH_3)OCH_3$ | H | H | O | $OCH_3$ | O | |
| $P(O)(CH_3)OCH_3$ | H | H | O | $CH_3$ | O | |
| $P(O)(OCH_3)_2$ | H | H | O | $OCH_3$ | O | |
| $P(O)(OCH_3)_2$ | H | H | O | $CH_3$ | O | |
| $P(O)(C_2H_5)OCH_3$ | H | H | O | $OCH_3$ | O | |
| $P(O)(C_2H_5)OCH_3$ | H | H | O | $CH_3$ | O | |
| $P(S)(CH_3)SCH_3$ | H | H | O | $OCH_3$ | O | |
| $P(S)(CH_3)SCH_3$ | H | H | O | $CH_3$ | O | |
| $P(S)(SCH_3)_2$ | H | H | O | $OCH_3$ | O | |
| $P(S)(SCH_3)_2$ | H | H | O | $CH_3$ | O | |
| $CH_2C(O)H$ | H | H | O | $OCH_3$ | O | |
| $CH_2C(O)H$ | H | H | O | $CH_3$ | O | |
| $CH_2C(O)CH_3$ | H | H | O | $OCH_3$ | O | |
| $CH_2C(O)CH_3$ | H | H | O | $CH_3$ | O | |
| $CH(Cl)CH_2CN$ | H | H | O | $OCH_3$ | O | |
| $CH(Cl)CH_2CN$ | H | H | O | $CH_3$ | O | |
| $CH(CH_3)CH_2NO_2$ | H | H | O | $OCH_3$ | O | |
| $CH(CH_3)CH_2NO_2$ | H | H | O | $CH_3$ | O | |
| $(CH_2)_2OCH_2CF_3$ | H | H | O | $OCH_3$ | O | |
| $(CH_2)_2OCH_2CF_3$ | H | H | O | $CH_3$ | O | |
| $(CH_2)_2OCH_2CCl_3$ | H | H | O | $OCH_3$ | O | |
| $(CH_2)_2OCH_2CCl_3$ | H | H | O | $CH_3$ | O | |
| $(CH_2)_2SCF_2H$ | H | H | O | $OCH_3$ | O | |
| $(CH_2)_2SCF_2H$ | H | H | O | $CH_3$ | O | |
| $(CH_2)_2SCF_2CF_2H$ | H | H | O | $OCH_3$ | O | |

TABLE I-continued

General Structure

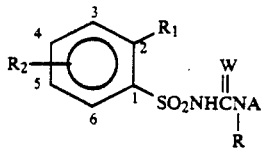

A = A-1

| $R_1$ | $R_2$ | R | W | X | Y | m.p. (°C.) |
|---|---|---|---|---|---|---|
| $(CH_2)_2SCF_2CF_2H$ | H | H | O | $CH_3$ | O | |
| $CH_2CH{=}CHCH_2Cl$ | H | H | O | $OCH_3$ | O | |
| $CH_2CH{=}CHCH_2Cl$ | H | H | O | $CH_3$ | O | |
| $CHCH{=}CBr_2$ | H | H | O | $OCH_3$ | O | |
| $CHCH{=}CBr_2$ | H | H | O | $CH_3$ | O | |
| $CHCH{=}CCH_2F$ | H | H | O | $OCH_3$ | O | |
| $CHCH{=}CCH_2F$ | H | H | O | $CH_3$ | O | |
| $CH{=}CHCH_2OCH_3$ | H | H | O | $OCH_3$ | O | |
| $CH{=}CHCH_2OCH_3$ | H | H | O | $CH_3$ | O | |
| $CH{=}CHCN$ | H | H | H | O | $OCH_3$ | O |
| $CH{=}CHCN$ | H | H | O | $CH_3$ | O | |
| $CH{=}CHCH_2OH$ | H | H | O | $OCH_3$ | O | |
| $CH{=}CHCH_2OH$ | H | H | O | $CH_3$ | O | |
| $CH{=}CHCH_2NO_2$ | H | H | O | $OCH_3$ | O | |
| $CH{=}CHCH_2NO_2$ | H | H | O | $CH_3$ | O | |
| $CH{=}CHCH_2SCH_3$ | H | H | O | $OCH_3$ | O | |
| $CH{=}CHCH_2SCH_3$ | H | H | O | $CH_3$ | O | |
| $CH_2CH{=}CHCH_2SO_2CH_3$ | H | H | O | $OCH_3$ | O | |
| $CH_2CH{=}CHCH_2SO_2CH_3$ | H | H | O | $CH_3$ | O | |
| $SCF_2H$ | H | H | O | H | O | |
| $SCF_2H$ | H | H | O | $CH_3$ | O | 184–189 |
| $SCF_2H$ | H | H | O | $C_2H_5$ | O | |
| $SCF_2H$ | H | H | O | $OCH_3$ | O | |
| $SCF_2H$ | H | H | O | $OC_2H_5$ | O | |
| $SCF_2H$ | H | H | O | Cl | O | |
| $SCF_2H$ | H | H | O | $OCF_2H$ | O | |
| $SCF_2H$ | H | H | O | $SCH_3$ | O | |
| $SCF_2H$ | H | H | O | $N(CH_3)_2$ | O | |
| $SCF_2H$ | H | H | O | H | $CH_2$ | |
| $SCF_2H$ | H | H | O | $CH_3$ | $CH_2$ | |
| $SCF_2H$ | H | H | O | $C_2H_5$ | $CH_2$ | |
| $SCF_2H$ | H | H | O | $OCH_3$ | $CH_2$ | |
| $SCF_2H$ | H | H | O | $OC_2H_5$ | $CH_2$ | |
| $SCF_2H$ | H | H | O | Cl | $CH_2$ | |
| $SCF_2H$ | H | H | O | $OCF_2H$ | $CH_2$ | |
| $SCF_2H$ | H | H | O | $SCH_3$ | $CH_2$ | |
| $SCF_2H$ | H | H | O | $N(CH_3)_2$ | $CH_2$ | |
| $SCF_2H$ | 6-$CH_3$ | H | O | $OCH_3$ | $CH_2$ | |
| $SCF_2H$ | 6-$CH_3$ | H | O | $OCH_3$ | O | |
| $SCF_2H$ | 6-$CH_3$ | H | O | $OCF_2H$ | O | |
| $S(CH_2)_2Cl$ | H | H | O | $CH_3$ | O | |
| $S(CH_2)_2Cl$ | H | H | O | $OCH_3$ | O | |
| $S(CH_2)_2Cl$ | H | H | O | $OCH_3$ | $CH_2$ | |
| $SCCl{=}CHCl$ | H | H | O | $OCH_3$ | $CH_2$ | |
| $SCCl{=}CHCl$ | H | H | O | $OCH_3$ | O | |
| $SCH_2CCl{=}CHCl$ | H | H | O | $OCH_3$ | O | |
| $SCH_2CCl{=}CHCl$ | H | H | O | $CH_3$ | O | |
| $SCF_2CF_2H$ | H | H | O | $OCH_3$ | O | |
| $SCF_2CF_2H$ | H | H | O | $CH_3$ | O | |
| $SCF_2CF_2H$ | H | H | O | $OCH_3$ | $CH_2$ | |
| $S(CH_2)_2Cl$ | H | H | O | $OCH_3$ | O | |
| $S(CH_2)_2Cl$ | H | H | O | $CH_3$ | O | |
| $SCH_2CCl_3$ | H | H | O | $OCH_3$ | O | |
| $SCH_2CCl_3$ | H | H | O | $CH_3$ | O | |
| $S(CH_2)_2OCH_3$ | H | H | O | $OCH_3$ | O | |
| $S(CH_2)_2OCH_3$ | H | H | O | $CH_3$ | O | |
| $S(CH_2)_3OCH_3$ | H | H | O | $OCH_3$ | O | |
| $S(CH_2)_3OCH_3$ | H | H | O | $CH_3$ | O | |
| $S(CH_2)_2OC_2H_5$ | H | H | O | $OCH_3$ | O | |
| $S(CH_2)_2OC_2H_5$ | H | H | O | $CH_3$ | O | |
| $S(CH_2)_2SCH_3$ | H | H | O | $OCH_3$ | O | |
| $S(CH_2)_2SCH_3$ | H | H | O | $CH_3$ | O | |
| $S(CH_2)_2SC_2H_5$ | H | H | O | $OCH_3$ | O | |
| $S(CH_2)_2SC_2H_5$ | H | H | O | $CH_3$ | O | |
| $S(CH_2)_2SOCH_3$ | H | H | O | $OCH_3$ | O | |
| $S(CH_2)_2SOCH_3$ | H | H | O | $CH_3$ | O | |
| $S(CH_2)_2SO_2C_2H_5$ | H | H | O | $OCH_3$ | O | |
| $S(CH_2)_2SO_2C_2H_5$ | H | H | O | $CH_3$ | O | |
| $S(CH_2)_2O(CH_2)_2Cl$ | H | H | O | $OCH_3$ | O | |
| $S(CH_2)_2O(CH_2)_2Cl$ | H | H | O | $CH_3$ | O | |

TABLE I-continued

General Structure

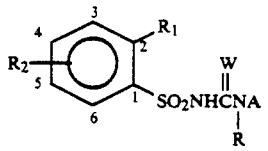

A = A-1

| $R_1$ | $R_2$ | R | W | X | Y | m.p. (°C.) |
|---|---|---|---|---|---|---|
| $S(CH_2)_2OCH_2CF_3$ | H | H | O | $OCH_3$ | O | |
| $S(CH_2)_2OCH_2CF_3$ | H | H | O | $CH_3$ | O | |
| $S(CH_2)_3O(CH_2)_2F$ | H | H | O | $OCH_3$ | O | |
| $S(CH_2)_3O(CH_2)_2F$ | H | H | O | $CH_3$ | O | |
| $S(CH_2)_2OCH_2CHF_2$ | H | H | O | $OCH_3$ | O | |
| $S(CH_2)_2OCH_2CHF_2$ | H | H | O | $CH_3$ | O | |
| $S(CH_2)_2S(CH_2)_2Cl$ | H | H | O | $OCH_3$ | O | |
| $S(CH_2)_2S(CH_2)_2Cl$ | H | H | O | $CH_3$ | O | |
| $S(CH_2)_2SO(CH_2)_2Cl$ | H | H | O | $OCH_3$ | O | |
| $S(CH_2)_2SO(CH_2)_2Cl$ | H | H | O | $CH_3$ | O | |
| $S(CH_2)SO_2(CH_2)_2Cl$ | H | H | O | $OCH_3$ | O | |
| $S(CH_2)SO_2(CH_2)_2Cl$ | H | H | O | $CH_3$ | O | |
| $S(CH_2)_2OH$ | H | H | O | $OCH_3$ | O | |
| $S(CH_2)_2OH$ | H | H | O | $CH_3$ | O | |
| $SCH_2CN$ | H | H | O | $OCH_3$ | O | |
| $SCH_2CN$ | H | H | O | $CH_3$ | O | |
| $SCH(CH_3)CN$ | H | H | O | $OCH_3$ | O | |
| $SCH(CH_3)CN$ | H | H | O | $CH_3$ | O | |
| $S(CH_2)_2NH_2$ | H | H | O | $OCH_3$ | O | |
| $S(CH_2)_2NH_2$ | H | H | O | $CH_3$ | O | |
| $S(CH_2)_3N(CH_3)_2$ | H | H | O | $OCH_3$ | O | |
| $S(CH_2)_3N(CH_3)_2$ | H | H | O | $CH_3$ | O | |
| $S(CH_2)_2NHCH_3$ | H | H | O | $OCH_3$ | O | |
| $S(CH_2)_2NHCH_3$ | H | H | O | $CH_3$ | O | |
| $SCH_2C_6H_5$ | H | H | O | $OCH_3$ | O | |
| $SCH_2C_6H_5$ | H | H | O | $CH_3$ | O | |
| $SCH_2CCl{=}CHCl$ | H | H | O | $OCH_3$ | O | |
| $SCH_2CCl{=}CHCl$ | H | H | O | $CH_3$ | O | |
| $SCH_2CH{=}CHCl$ | H | H | O | $OCH_3$ | O | |
| $SCH_2CH{=}CHCl$ | H | H | O | $CH_3$ | O | |
| $SCH_2CH{=}CHBr$ | H | H | O | $OCH_3$ | O | |
| $SCH_2CH{=}CHBr$ | H | H | O | $CH_3$ | O | |
| $SCH_2C{=}CH{-}CH_2Cl$ | H | H | O | $OCH_3$ | O | |
| $SCH_2C{=}CH{-}CH_2Cl$ | H | H | O | $CH_3$ | O | |
| $SCH_2CH{=}CHCH_2SCH_3$ | H | H | O | $OCH_3$ | O | |
| $SCH_2CH{=}CHCH_2SCH_3$ | H | H | O | $CH_3$ | O | |
| $SCH_2CH{=}CHS(O)CH_3$ | H | H | O | $OCH_3$ | O | |
| $SCH_2CH{=}CHS(O)CH_3$ | H | H | O | $CH_3$ | O | |
| $SCH_2CH{=}CHCH_2SO_2CH_3$ | H | H | O | $OCH_3$ | O | |
| $SCH_2CH{=}CHCH_2SO_2CH_3$ | H | H | O | $CH_3$ | O | |
| $SCH_2CH{=}CHCH_2OH$ | H | H | O | $OCH_3$ | O | |
| $SCH_2CH{=}CHCH_2OH$ | H | H | O | $CH_3$ | O | |
| $SCH{=}CH{-}CN$ | H | H | O | $OCH_3$ | O | |
| $SCH{=}CH{-}CN$ | H | H | O | $CH_3$ | O | |
| $SCH{=}CHCH_2NH_2$ | H | H | O | $OCH_3$ | O | |
| $SCH{=}CHCH_2NH_2$ | H | H | O | $CH_3$ | O | |
| $SCH_2CH{=}CHN(CH_3)_2$ | H | H | O | $OCH_3$ | O | |
| $SCH_2CH{=}CHN(CH_3)_2$ | H | H | O | $CH_3$ | O | |
| $SCH_2CH{=}CHC_6H_5$ | H | H | O | $OCH_3$ | O | |
| $SCH_2CH{=}CHC_6H_5$ | H | H | O | $CH_3$ | O | |
| $SCH_2C{\equiv}C{-}CH_3$ | H | H | O | $OCH_3$ | O | |
| $SCH_2C{\equiv}C{-}CH_3$ | H | H | O | $CH_3$ | O | |
| $SCH_2C{\equiv}CH$ | H | H | O | $OCH_3$ | O | |
| $SCH_2C{\equiv}CH$ | H | H | O | $CH_3$ | O | |
| $SC{\equiv}CH$ | H | H | O | $OCH_3$ | O | |
| $SC{\equiv}CH$ | H | H | O | $CH_3$ | O | |
| $OCF_2H$ | 5-F | H | O | $OCH_3$ | O | |
| $OCF_2H$ | 5-F | H | O | $CH_3$ | O | |
| $SCF_2H$ | 5-F | H | O | $OCH_3$ | O | |
| $SCF_2H$ | 5-F | H | O | $CH_3$ | O | |
| $OCF_2H$ | 5-Cl | H | O | $OCH_3$ | O | |
| $OCF_2H$ | 5-Cl | H | O | $CH_3$ | O | |
| $SCF_2H$ | 5-Cl | H | O | $OCH_3$ | O | |
| $SCF_2H$ | 5-Cl | H | O | $CH_3$ | O | |
| $OCF_2H$ | 5-Br | H | O | $OCH_3$ | O | |
| $OCF_2H$ | 5-Br | H | O | $CH_3$ | O | |
| $SCF_2H$ | 5-$CF_3$ | H | O | $OCH_3$ | O | |
| $SCF_2H$ | 5-$CF_3$ | H | O | $CH_3$ | O | |
| $SCF_2H$ | 5-CN | H | O | $OCH_3$ | O | |
| $SCF_2H$ | 5-CN | H | O | $CH_3$ | O | |

TABLE I-continued

General Structure

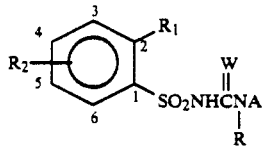

A = A-1

| $R_1$ | $R_2$ | R | W | X | Y | m.p. (°C.) |
|---|---|---|---|---|---|---|
| $SCF_2H$ | 5-$NO_2$ | H | O | $OCH_3$ | O | |
| $SCF_2H$ | 5-$NO_2$ | H | O | $CH_3$ | O | |
| $OCF_2H$ | 5-$CH_3$ | H | O | $OCH_3$ | O | |
| $OCF_2H$ | 5-$CH_3$ | H | O | $CH_3$ | O | |
| $OCF_2H$ | 5-$C_2H_5$ | H | O | $OCH_3$ | O | |
| $OCF_2H$ | 5-$C_2H_5$ | H | O | $CH_3$ | O | |
| $OCF_2H$ | 5-$OCH_3$ | H | O | $OCH_3$ | O | |
| $OCF_2H$ | 5-$OCH_3$ | H | O | $CH_3$ | O | |
| $OCF_2H$ | 5-$OC_2H_5$ | H | O | $OCH_3$ | O | |
| $OCF_2H$ | 5-$OC_2H_5$ | H | O | $CH_3$ | O | |
| $OCF_2H$ | 5-$SCH_3$ | H | O | $OCH_3$ | O | |
| $OCF_2H$ | 5-$SCH_3$ | H | O | $CH_3$ | O | |
| $OCF_2H$ | 5-$SC_2H_5$ | H | O | $OCH_3$ | O | |
| $OCF_2H$ | 5-$SC_2H_5$ | H | O | $CH_3$ | O | |
| $OCF_2H$ | 5-$CH_2Cl$ | H | O | $OCH_3$ | O | |
| $OCF_2H$ | 5-$CH_2Cl$ | H | O | $CH_3$ | O | |
| $OCF_2H$ | 5-$(CH_2)_2Cl$ | H | O | $OCH_3$ | O | |
| $OCF_2H$ | 5-$(CH_2)_2Cl$ | H | O | $CH_3$ | O | |
| $OCF_2H$ | 5-$OCF_2H$ | H | O | $OCH_3$ | O | |
| $OCF_2H$ | 5-$OCF_2H$ | H | O | $CH_3$ | O | |
| $OCF_2CF_2H$ | 5-$OCF_2CF_2H$ | H | O | $OCH_3$ | O | |
| $OCF_2CF_2H$ | 5-$OCF_2CF_2H$ | H | O | $CH_3$ | O | |
| $OCF_2H$ | 5-$CH_2OCH_3$ | H | O | $OCH_3$ | O | |
| $OCF_2H$ | 5-$CH_2OCH_3$ | H | O | $CH_3$ | O | |
| $SCF_2H$ | 5-$CH_2OCH_3$ | H | O | $OCH_3$ | O | |
| $SCF_2H$ | 5-$CH_2OCH_3$ | H | O | $CH_3$ | O | |
| $SCF_2CF_2H$ | 5-$SCF_2CF_2H$ | H | O | $OCH_3$ | O | |
| $SCF_2CF_2H$ | 5-$SCF_2CF_2H$ | H | O | $CH_3$ | O | |
| $SOCF_2H$ | 5-$SOCF_2H$ | H | O | $OCH_3$ | O | |
| $SOCF_2H$ | 5-$SOCF_2H$ | H | O | $CH_3$ | O | |
| $SO_2CF_2H$ | 5-$SO_2CF_2H$ | H | O | $OCH_3$ | O | |
| $SO_2CF_2H$ | 5-$SO_2CF_2H$ | H | O | $CH_3$ | O | |
| $OCF_2H$ | 5-$CH_2SCH_3$ | H | O | $OCH_3$ | O | |
| $OCF_2H$ | 5-$CH_2SCH_3$ | H | O | $CH_3$ | O | |
| $OCF_2H$ | 5-$OCH_2CH{=}CH_3$ | H | O | $OCH_3$ | O | |
| $OCF_2H$ | 5-$OCH_2CH{=}CH_2$ | H | O | $CH_3$ | O | |
| $OCF_2H$ | 5-$OCH_2C{\equiv}CH$ | H | O | $OCH_3$ | O | |
| $OCF_2H$ | 5-$OCH_2C{\equiv}CH$ | H | O | $CH_3$ | O | |
| $OCF_2H$ | 6-Cl | H | O | $OCH_3$ | O | |
| $OCF_2H$ | 6-Cl | H | O | $CH_3$ | O | |
| $OCF_2H$ | 3-Cl | H | O | $OCH_3$ | O | |
| $OCF_2H$ | 3-Cl | H | O | $CH_3$ | O | |
| $OCF_2H$ | 3-$CH_3$ | H | O | $OCH_3$ | O | |
| $OCF_2H$ | 3-$CH_3$ | H | O | $CH_3$ | O | |
| $OCF_2H$ | 6-F | H | O | $OCH_3$ | O | |
| $OCF_2H$ | 6-F | H | O | $CH_3$ | O | |
| $OCF_2H$ | 3-F | H | O | $OCH_3$ | O | |
| $OCF_2H$ | 3-F | H | O | $CH_3$ | O | |
| $OCF_2H$ | 4-F | H | O | $OCH_3$ | O | |
| $OCF_2H$ | 4-F | H | O | $CH_3$ | O | |
| $OCF_2H$ | 6-$NO_2$ | H | O | $OCH_3$ | O | |
| $OCF_2H$ | 6-$NO_2$ | H | O | $CH_3$ | O | |
| $OCF_2H$ | 6-$OCH_3$ | H | O | $OCH_3$ | O | |
| $OCF_2H$ | 6-$OCH_3$ | H | O | $CH_3$ | O | |
| $OCF_2H$ | H | $CH_3$ | O | $OCH_3$ | O | |
| $OCF_2H$ | H | $CH_3$ | O | $CH_3$ | O | |
| $SCF_2H$ | H | $CH_3$ | O | $OCH_3$ | O | |
| $SCF_2H$ | H | $CH_3$ | O | $CH_3$ | O | |
| $OCF_2H$ | H | H | S | $OCH_3$ | O | |
| $OCF_2H$ | H | H | S | $CH_3$ | O | |
| $SCF_2H$ | H | H | S | $OCH_3$ | O | |
| $SCF_2H$ | H | H | S | $CH_3$ | O | |
| $SCF_2H$ | H | H | S | $OCH_3$ | $CH_2$ | |
| $SCF_2H$ | H | H | S | $CH_3$ | $CH_2$ | |
| $OCF_2H$ | H | H | S | $OCH_3$ | $CH_2$ | |
| $OCF_2H$ | H | H | S | $CH_3$ | $CH_2$ | |

TABLE II

A = A-2

| $R_1$ | $R_2$ | R | W | X | m.p. (°C.) |
|---|---|---|---|---|---|
| $OCF_2H$ | H | H | O | H | |
| $OCF_2H$ | H | H | O | $CH_3$ | |
| $OCF_2H$ | H | H | O | $C_2H_5$ | |
| $OCF_2H$ | H | H | O | $OCH_3$ | |
| $OCF_2H$ | H | H | O | $OC_2H_5$ | |
| $OCF_2H$ | H | H | O | Cl | |
| $OCF_2H$ | H | H | O | $OCF_2H$ | |
| $OCF_2H$ | H | H | O | $SCH_3$ | |
| $OCF_2H$ | H | H | O | $N(CH_3)_2$ | |
| $OCF_2H$ | 6-$CH_3$ | H | O | $OCH_3$ | |
| $OCF_2H$ | 6-$CH_3$ | H | O | $OCF_2H$ | |
| $OCF_2H$ | 5-$CH_3$ | H | O | $OCH_3$ | |
| $OCF_2H$ | 5-$CH_3$ | H | O | $CH_3$ | |
| $O(CH_2)_2Cl$ | H | H | O | $CH_3$ | |
| $O(CH_2)_2Cl$ | H | H | O | $OCH_3$ | |
| $OCCl{=}CHCl$ | H | H | O | $OCH_3$ | |
| $OCCl{=}CHCl$ | H | H | O | $CH_3$ | |
| $OCH_2CCl{=}CHCl$ | H | H | O | $OCH_3$ | |
| $OCH_2CCl{=}CHCl$ | H | H | O | $CH_3$ | |
| $OCF_2CF_2H$ | H | H | O | $OCH_3$ | |
| $OCF_2CF_2H$ | H | H | O | $CH_3$ | |
| $O(CH_2)_2Cl$ | H | H | O | $OCH_3$ | |
| $O(CH_2)_2Cl$ | H | H | O | $CH_3$ | |
| $OCH_2CCl_3$ | H | H | O | $OCH_3$ | |
| $OCH_2CCl_3$ | H | H | O | $CH_3$ | |
| $O(CH_2)_2OCH_3$ | H | H | O | $OCH_3$ | |
| $O(CH_2)_2OCH_3$ | H | H | O | $CH_3$ | |
| $O(CH_2)_3OCH_3$ | H | H | O | $OCH_3$ | |
| $O(CH_2)_3OCH_3$ | H | H | O | $CH_3$ | |
| $O(CH_2)_2OC_2H_5$ | H | H | O | $OCH_3$ | |
| $O(CH_2)_2OC_2H_5$ | H | H | O | $CH_3$ | |
| $O(CH_2)_2SCH_3$ | H | H | O | $OCH_3$ | |
| $O(CH_2)_2SCH_3$ | H | H | O | $CH_3$ | |
| $O(CH_2)_2SC_2H_5$ | H | H | O | $OCH_3$ | |
| $O(CH_2)_2SC_2H_5$ | H | H | O | $CH_3$ | |
| $O(CH_2)_2SOCH_3$ | H | H | O | $OCH_3$ | |
| $O(CH_2)_2SOCH_3$ | H | H | O | $CH_3$ | |
| $O(CH_2)_2SO_2C_2H_5$ | H | H | O | $OCH_3$ | |
| $O(CH_2)_2SO_2C_2H_5$ | H | H | O | $CH_3$ | |
| $O(CH_2)_2O(CH_2)_2Cl$ | H | H | O | $OCH_3$ | |
| $O(CH_2)_2O(CH_2)_2Cl$ | H | H | O | $CH_3$ | |
| $O(CH_2)_2OCH_2CF_3$ | H | H | O | $OCH_3$ | |
| $O(CH_2)_2OCH_2CF_3$ | H | H | O | $CH_3$ | |
| $O(CH_2)_3O(CH_2)_2F$ | H | H | O | $OCH_3$ | |
| $O(CH_2)_3O(CH_2)_2F$ | H | H | O | $CH_3$ | |
| $O(CH_2)_2OCH_2CHF_2$ | H | H | O | $OCH_3$ | |
| $O(CH_2)_2OCH_2CHF_2$ | H | H | O | $CH_3$ | |
| $O(CH_2)_2S(CH_2)_2Cl$ | H | H | O | $OCH_3$ | |
| $O(CH_2)_2S(CH_2)_2Cl$ | H | H | O | $CH_3$ | |
| $O(CH_2)_2SO(CH_2)_2Cl$ | H | H | O | $OCH_3$ | |
| $O(CH_2)_2SO(CH_2)_2Cl$ | H | H | O | $CH_3$ | |
| $O(CH_2)SO_2(CH_2)_2Cl$ | H | H | O | $OCH_3$ | |
| $O(CH_2)SO_2(CH_2)_2Cl$ | H | H | O | $CH_3$ | |
| $O(CH_2)_2OH$ | H | H | O | $OCH_3$ | |
| $O(CH_2)_2OH$ | H | H | O | $CH_3$ | |
| $OCH_2CN$ | H | H | O | $OCH_3$ | |
| $OCH_2CN$ | H | H | O | $CH_3$ | |
| $OCH(CH_3)CN$ | H | H | O | $OCH_3$ | |
| $OCH(CH_3)CN$ | H | H | O | $CH_3$ | |
| $O(CH_2)_2NH_2$ | H | H | O | $OCH_3$ | |
| $O(CH_2)_2NH_2$ | H | H | O | $CH_3$ | |
| $O(CH_2)_3N(CH_3)_2$ | H | H | O | $OCH_3$ | |
| $O(CH_2)_3N(CH_3)_2$ | H | H | O | $CH_3$ | |
| $O(CH_2)_2NHCH_3$ | H | H | O | $OCH_3$ | |
| $O(CH_2)_2NHCH_3$ | H | H | O | $CH_3$ | |
| $OCH_2C_6H_5$ | H | H | O | $OCH_3$ | |
| $OCH_2C_6H_5$ | H | H | O | $CH_3$ | |
| $OCH_2CCl{=}CHCl$ | H | H | O | $OCH_3$ | |
| $OCH_2CCl{=}CHCl$ | H | H | O | $CH_3$ | |
| $OCH_2CH{=}CHCl$ | H | H | O | $OCH_3$ | |
| $OCH_2CH{=}CHCl$ | H | H | O | $CH_3$ | |
| $OCH_2CH{=}CHBr$ | H | H | O | $OCH_3$ | |
| $OCH_2CH{=}CHBr$ | H | H | O | $CH_3$ | |
| $OCH_2C{=}CH{-}CH_2Cl$ | H | H | O | $OCH_3$ | |
| $OCH_2C{=}CH{-}CH_2Cl$ | H | H | O | $CH_3$ | |
| $OCH_2CH{=}CHCH_2SCH_3$ | H | H | O | $OCH_3$ | |
| $OCH_2CH{=}CHCH_2SCH_3$ | H | H | O | $CH_3$ | |
| $OCH_2CH{=}CHS(O)CH_3$ | H | H | O | $OCH_3$ | |

TABLE II-continued

A = A-2

| $R_1$ | $R_2$ | R | W | X | m.p. (°C.) |
|---|---|---|---|---|---|
| $OCH_2CH{=}CHS(O)CH_3$ | H | H | O | $CH_3$ | |
| $OCH_2CH{=}CHCH_2SO_2CH_3$ | H | H | O | $OCH_3$ | |
| $OCH_2CH{=}CHCH_2SO_2CH_3$ | H | H | O | $CH_3$ | |
| $OCH_2CH{=}CHCH_2OH$ | H | H | O | $OCH_3$ | |
| $OCH_2CH{=}CHCH_2OH$ | H | H | O | $CH_3$ | |
| $OCH{=}CH{-}CN$ | H | H | O | $OCH_3$ | |
| $OCH{=}CH{-}CN$ | H | H | O | $CH_3$ | |
| $OCH{=}CHCH_2NH_2$ | H | H | O | $OCH_3$ | |
| $OCH{=}CHCH_2NH_2$ | H | H | O | $CH_3$ | |
| $OCH_2CH{=}CHN(CH_3)_2$ | H | H | O | $OCH_3$ | |
| $OCH_2CH{=}CHN(CH_3)_2$ | H | H | O | $CH_3$ | |
| $OCH_2CH{=}CHC_6H_5$ | H | H | O | $OCH_3$ | |
| $OCH_2CH{=}CHC_6H_5$ | H | H | O | $CH_3$ | |
| $OCH_2C{\equiv}C{-}CH_3$ | H | H | O | $OCH_3$ | |
| $OCH_2C{\equiv}C{-}CH_3$ | H | H | O | $CH_3$ | |
| $OCH_2C{\equiv}CH$ | H | H | O | $OCH_3$ | |
| $OCH_2C{\equiv}CH$ | H | H | O | $CH_3$ | |
| $C{\equiv}CH$ | H | H | O | $OCH_3$ | |
| $C{\equiv}CH$ | H | H | O | $CH_3$ | |
| $C{\equiv}CCH_3$ | H | H | O | $OCH_3$ | |
| $C{\equiv}CCH_3$ | H | H | O | $CH_3$ | |
| $C{\equiv}CC_2H_5$ | H | H | O | $OCH_3$ | |
| $C{\equiv}CC_2H_5$ | H | H | O | $CH_3$ | |
| $C{\equiv}CCH_2Cl$ | H | H | O | $OCH_3$ | |
| $C{\equiv}CCH_2Cl$ | H | H | O | $CH_3$ | |
| $C{\equiv}CCHCl_2$ | H | H | O | $OCH_3$ | |
| $C{\equiv}CCHCl_2$ | H | H | O | $CH_3$ | |
| $C{\equiv}C{-}CH_2{-}CCl_3$ | H | H | O | $OCH_3$ | |
| $C{\equiv}C{-}CH_2{-}CCl_3$ | H | H | O | $CH_3$ | |
| $C{\equiv}CCH_2OH$ | H | H | O | $OCH_3$ | |
| $C{\equiv}CCH_2OH$ | H | H | O | $CH_3$ | |
| $C{\equiv}CCH_2OCH_3$ | H | H | O | $OCH_3$ | |
| $C{\equiv}CCH_2OCH_3$ | H | H | O | $CH_3$ | |
| $C{\equiv}CCH_2OC_2H_5$ | H | H | O | $OCH_3$ | |
| $C{\equiv}CCH_2OC_2H_5$ | H | H | O | $CH_3$ | |
| $C{\equiv}CCH_2SC_2H_5$ | H | H | O | $OCH_3$ | |
| $C{\equiv}CCH_2SC_2H_5$ | H | H | O | $CH_3$ | |
| $C{\equiv}CCH_2OCH_2CCl_3$ | H | H | O | $OCH_3$ | |
| $C{\equiv}CCH_2OCH_2CCl_3$ | H | H | O | $CH_3$ | |
| $C{\equiv}CCH_2CN$ | H | H | O | $OCH_3$ | |
| $C{\equiv}CCH_2CN$ | H | H | O | $CH_3$ | |
| $C{\equiv}CCH_2CO_2CH_3$ | H | H | O | $OCH_3$ | |
| $C{\equiv}CCH_2CO_2CH_3$ | H | H | O | $CH_3$ | |
| $C{\equiv}CCH(CH_3)CO_2C_2H_5$ | H | H | O | $OCH_3$ | |
| $C{\equiv}CCH(CH_3)CO_2C_2H_5$ | H | H | O | $CH_3$ | |
| $C{\equiv}CCH_2$—cyclopropyl | H | H | O | $OCH_3$ | |
| $C{\equiv}CCH_2$—cyclopropyl | H | H | O | $CH_3$ | |
| $C{\equiv}CCH_2C_6H_5$ | H | H | O | $OCH_3$ | |
| $C{\equiv}CCH_2C_6H_5$ | H | H | O | $CH_3$ | |
| $C{\equiv}C$—cyclopentyl | H | H | O | $OCH_3$ | |
| $C{\equiv}C$—cyclopentyl | H | H | O | $CH_3$ | |
| $C{\equiv}C$—cyclohexyl | H | H | O | $OCH_3$ | |
| $C{\equiv}C$—cyclohexyl | H | H | O | $CH_3$ | |
| $C{\equiv}CC_6H_5$ | H | H | O | $OCH_3$ | |
| $C{\equiv}CC_6H_5$ | H | H | O | $CH_3$ | |
| $N_3$ | H | H | O | $OCH_3$ | |
| $N_3$ | H | H | O | $CH_3$ | |
| $P(O)(CH_3)OCH_3$ | H | H | O | $OCH_3$ | |
| $P(O)(CH_3)OCH_3$ | H | H | O | $CH_3$ | |
| $P(O)(OCH_3)_2$ | H | H | O | $OCH_3$ | |
| $P(O)(OCH_3)_2$ | H | H | O | $CH_3$ | |
| $P(O)(C_2H_5)OCH_3$ | H | H | O | $OCH_3$ | |
| $P(O)(C_2H_5)OCH_3$ | H | H | O | $CH_3$ | |
| $P(S)(CH_3)SCH_3$ | H | H | O | $OCH_3$ | |
| $P(S)(CH_3)SCH_3$ | H | H | O | $CH_3$ | |
| $P(S)(SCH_3)_2$ | H | H | O | $OCH_3$ | |
| $P(S)(SCH_3)_2$ | H | H | O | $CH_3$ | |
| $CH_2C(O)H$ | H | H | O | $OCH_3$ | |
| $CH_2C(O)H$ | H | H | O | $CH_3$ | |
| $CH_2C(O)CH_3$ | H | H | O | $OCH_3$ | |
| $CH_2C(O)CH_3$ | H | H | O | $CH_3$ | |
| $CH(Cl)CH_2CN$ | H | H | O | $OCH_3$ | |
| $CH(Cl)CH_2CN$ | H | H | O | $CH_3$ | |
| $CH(CH_3)CH_2NO_2$ | H | H | O | $OCH_3$ | |
| $CH(CH_3)CH_2NO_2$ | H | H | O | $CH_3$ | |
| $(CH_2)_2OCH_2CF_3$ | H | H | O | $OCH_3$ | |
| $(CH_2)_2OCH_2CF_3$ | H | H | O | $CH_3$ | |
| $(CH_2)_2OCH_2CCl_3$ | H | H | O | $OCH_3$ | |

TABLE II-continued

A = A-2

| $R_1$ | $R_2$ | R | W | X | m.p. (°C.) |
|---|---|---|---|---|---|
| $(CH_2)_2OCH_2CCl_3$ | H | H | O | $CH_3$ | |
| $(CH_2)_2SCF_2H$ | H | H | O | $OCH_3$ | |
| $(CH_2)_2SCF_2H$ | H | H | O | $CH_3$ | |
| $(CH_2)_2SCF_2CF_2H$ | H | H | O | $OCH_3$ | |
| $(CH_2)_2SCF_2CF_2H$ | H | H | O | $CH_3$ | |
| $CH_2CH{=}CHCH_2Cl$ | H | H | O | $OCH_3$ | |
| $CH_2CH{=}CHCH_2Cl$ | H | H | O | $CH_3$ | |
| $CHCH{=}CBr_2$ | H | H | O | $OCH_3$ | |
| $CHCH{=}CBr_2$ | H | H | O | $CH_3$ | |
| $CHCH{=}CCH_2F$ | H | H | O | $OCH_3$ | |
| $CHCH{=}CCH_2F$ | H | H | O | $CH_3$ | |
| $CH{=}CHCH_2OCH_3$ | H | H | O | $OCH_3$ | |

TABLE II-continued

A = A-2

| $R_1$ | $R_2$ | R | W | X | m.p. (°C.) |
|---|---|---|---|---|---|
| $CH{=}CHCH_2OCH_3$ | H | H | O | $CH_3$ | |
| $CH{=}CHCN$ | H | H | O | $OCH_3$ | |
| $CH{=}CHCN$ | H | H | O | $CH_3$ | |
| $CH{=}CHCH_2OH$ | H | H | O | $OCH_3$ | |
| $CH{=}CHCH_2OH$ | H | H | O | $CH_3$ | |
| $CH{=}CHCH_2NO_2$ | H | H | O | $OCH_3$ | |
| $CH{=}CHCH_2NO_2$ | H | H | O | $CH_3$ | |
| $CH{=}CHCH_2SCH_3$ | H | H | O | $OCH_3$ | |
| $CH{=}CHCH_2SCH_3$ | H | H | O | $CH_3$ | |
| $CH_2CH{=}CHCH_2SO_2CH_3$ | H | H | O | $OCH_3$ | |
| $CH_2CH{=}CHCH_2SO_2CH_3$ | H | H | O | $CH_3$ | |

TABLE III

A = A-3

| $R_1$ | $R_2$ | R | W | X | $Y_1$ | m.p. (°C.) |
|---|---|---|---|---|---|---|
| $OCCl{=}CHCl$ | H | H | O | H | $CH_3$ | |
| $OCCl{=}CHCl$ | H | H | O | $CH_3$ | $CH_3$ | |
| $OCCl{=}CHCl$ | H | H | O | $C_2H_5$ | $CH_3$ | |
| $OCCl{=}CHCl$ | H | H | O | $OCH_3$ | $CH_3$ | |
| $OCCl{=}CHCl$ | H | H | O | $OC_2H_5$ | $CH_3$ | |
| $OCCl{=}CHCl$ | H | H | O | Cl | $CH_3$ | |
| $OCCl{=}CHCl$ | H | H | O | $OCF_2H$ | $CH_3$ | |
| $OCCl{=}CHCl$ | H | H | O | $SCH_3$ | $CH_3$ | |
| $OCCl{=}CHCl$ | H | H | O | $N(CH_3)_2$ | $CH_3$ | |
| $OCCl{=}CHCl$ | H | H | O | H | $C_2H_5$ | |
| $OCCl{=}CHCl$ | H | H | O | $CH_3$ | $C_2H_5$ | |
| $OCCl{=}CHCl$ | H | H | O | $C_2H_5$ | $C_2H_5$ | |
| $OCCl{=}CHCl$ | H | H | O | $OCH_3$ | $C_2H_5$ | |
| $OCCl{=}CHCl$ | H | H | O | $OC_2H_5$ | $C_2H_5$ | |
| $OCCl{=}CHCl$ | H | H | O | Cl | $C_2H_5$ | |
| $OCCl{=}CHCl$ | H | H | O | $OCF_2H$ | $C_2H_5$ | |
| $OCCl{=}CHCl$ | H | H | O | $SCH_3$ | $C_2H_5$ | |
| $OCCl{=}CHCl$ | H | H | O | $N(CH_3)_2$ | $C_2H_5$ | |
| $OCCl{=}CHCl$ | H | H | O | H | H | |
| $OCCl{=}CHCl$ | H | H | O | $CH_3$ | H | |
| $OCCl{=}CHCl$ | H | H | O | $C_2H_5$ | H | |
| $OCCl{=}CHCl$ | H | H | O | $OCH_3$ | H | |
| $OCCl{=}CHCl$ | H | H | O | $OC_2H_5$ | H | |
| $OCCl{=}CHCl$ | H | H | O | Cl | H | |
| $OCCl{=}CHCl$ | H | H | O | $OCF_2H$ | H | |
| $OCCl{=}CHCl$ | H | H | O | $SCH_3$ | H | |
| $OCCl{=}CHCl$ | H | H | O | $N(CH_3)_2$ | H | |
| $OCCl{=}CHCl$ | 6-$CH_3$ | H | O | $OCH_3$ | H | |
| $OCCl{=}CHCl$ | 6-$CH_3$ | H | O | $OCH_3$ | $CH_3$ | |
| $OCCl{=}CHCl$ | 6-$CH_3$ | H | O | $OCF_2H$ | $CH_3$ | |
| $OCCl{=}CHCl$ | 5-$CH_3$ | H | O | $OCH_3$ | $CH_3$ | |
| $OCCl{=}CHCl$ | 5-$CH_3$ | H | O | $CH_3$ | $CH_3$ | |
| $O(CH_2)_2Cl$ | H | H | O | $CH_3$ | $CH_3$ | |
| $O(CH_2)_2Cl$ | H | H | O | $OCH_3$ | $CH_3$ | |
| $OCH_2CCl{=}CHCl$ | H | H | O | $OCH_3$ | $CH_3$ | |
| $OCH_2CCl{=}CHCl$ | H | H | O | $CH_3$ | $CH_3$ | |
| $O(CH_2)_2Cl$ | H | H | O | $OCH_3$ | $CH_3$ | |
| $O(CH_2)_2Cl$ | H | H | O | $CH_3$ | $CH_3$ | |
| $OCH_2CCl_3$ | H | H | O | $OCH_3$ | $CH_3$ | |
| $OCH_2CCl_3$ | H | H | O | $CH_3$ | $CH_3$ | |
| $O(CH_2)_2OCH_3$ | H | H | O | $OCH_3$ | $CH_3$ | |
| $O(CH_2)_2OCH_3$ | H | H | O | $CH_3$ | $CH_3$ | |
| $O(CH_2)_3OCH_3$ | H | H | O | $OCH_3$ | $CH_3$ | |
| $O(CH_2)_3OCH_3$ | H | H | O | $CH_3$ | $CH_3$ | |
| $O(CH_2)_2OC_2H_5$ | H | H | O | $OCH_3$ | $CH_3$ | |
| $O(CH_2)_2OC_2H_5$ | H | H | O | $CH_3$ | $CH_3$ | |
| $O(CH_2)_2SCH_3$ | H | H | O | $OCH_3$ | $CH_3$ | |
| $O(CH_2)_2SCH_3$ | H | H | O | $CH_3$ | $CH_3$ | |
| $O(CH_2)_2SC_2H_5$ | H | H | O | $OCH_3$ | $CH_3$ | |
| $O(CH_2)_2SC_2H_5$ | H | H | O | $CH_3$ | $CH_3$ | |
| $O(CH_2)_2SOCH_3$ | H | H | O | $OCH_3$ | $CH_3$ | |
| $O(CH_2)_2SOCH_3$ | H | H | O | $CH_3$ | $CH_3$ | |
| $O(CH_2)_2SO_2C_2H_5$ | H | H | O | $OCH_3$ | $CH_3$ | |
| $O(CH_2)_2SO_2C_2H_5$ | H | H | O | $CH_3$ | $CH_3$ | |
| $O(CH_2)_2O(CH_2)_2Cl$ | H | H | O | $OCH_3$ | $CH_3$ | |
| $O(CH_2)_2O(CH_2)_2Cl$ | H | H | O | $CH_3$ | $CH_3$ | |
| $O(CH_2)_2OCH_2CF_3$ | H | H | O | $OCH_3$ | $CH_3$ | |
| $O(CH_2)_2OCH_2CF_3$ | H | H | O | $CH_3$ | $CH_3$ | |
| $O(CH_2)_3O(CH_2)_2F$ | H | H | O | $OCH_3$ | $CH_3$ | |
| $O(CH_2)_3O(CH_2)_2F$ | H | H | O | $CH_3$ | $CH_3$ | |
| $O(CH_2)_2OCH_2CHF_2$ | H | H | O | $OCH_3$ | $CH_3$ | |

TABLE III-continued

| | A = A-3 | | | | | |
|---|---|---|---|---|---|---|
| $R_1$ | $R_2$ | R | W | X | $Y_1$ | m.p. (°C.) |
| $O(CH_2)_2OCH_2CHF_2$ | H | H | O | $CH_3$ | $CH_3$ | |
| $O(CH_2)_2S(CH_2)_2Cl$ | H | H | O | $OCH_3$ | $CH_3$ | |
| $O(CH_2)_2S(CH_2)_2Cl$ | H | H | O | $CH_3$ | $CH_3$ | |
| $O(CH_2)_2SO(CH_2)_2Cl$ | H | H | O | $OCH_3$ | $CH_3$ | |
| $O(CH_2)_2SO(CH_2)_2Cl$ | H | H | O | $CH_3$ | $CH_3$ | |
| $O(CH_2)SO_2(CH_2)_2Cl$ | H | H | O | $OCH_3$ | $CH_3$ | |
| $O(CH_2)SO_2(CH_2)_2Cl$ | H | H | O | $CH_3$ | $CH_3$ | |
| $O(CH_2)_2OH$ | H | H | O | $OCH_3$ | $CH_3$ | |
| $O(CH_2)_2OH$ | H | H | O | $CH_3$ | $CH_3$ | |
| $OCH_2CN$ | H | H | O | $OCH_3$ | $CH_3$ | |
| $OCH_2CN$ | H | H | O | $CH_3$ | $CH_3$ | |
| $OCH(CH_3)CN$ | H | H | O | $OCH_3$ | $CH_3$ | |
| $OCH(CH_3)CN$ | H | H | O | $CH_3$ | $CH_3$ | |
| $O(CH_2)_2NH_2$ | H | H | O | $OCH_3$ | $CH_3$ | |
| $O(CH_2)_2NH_2$ | H | H | O | $CH_3$ | $CH_3$ | |
| $O(CH_2)_3N(CH_3)_2$ | H | H | O | $OCH_3$ | $CH_3$ | |
| $O(CH_2)_3N(CH_3)_2$ | H | H | O | $CH_3$ | $CH_3$ | |
| $O(CH_2)_2NHCH_3$ | H | H | O | $OCH_3$ | $CH_3$ | |
| $O(CH_2)_2NHCH_3$ | H | H | O | $CH_3$ | $CH_3$ | |
| $OCH_2C_6H_5$ | H | H | O | $OCH_3$ | $CH_3$ | |
| $OCH_2C_6H_5$ | H | H | O | $CH_3$ | $CH_3$ | |
| $OCH_2CCl{=}CHCl$ | H | H | O | $OCH_3$ | $CH_3$ | |
| $OCH_2CCl{=}CHCl$ | H | H | O | $CH_3$ | $CH_3$ | |
| $OCH_2CH{=}CHCl$ | H | H | O | $OCH_3$ | $CH_3$ | |
| $OCH_2CH{=}CHCl$ | H | H | O | $CH_3$ | $CH_3$ | |
| $OCH_2CH{=}CHBr$ | H | H | O | $OCH_3$ | $CH_3$ | |
| $OCH_2CH{=}CHBr$ | H | H | O | $CH_3$ | $CH_3$ | |
| $OCH_2C{=}CH{-}CH_2Cl$ | H | H | O | $OCH_3$ | $CH_3$ | |
| $OCH_2C{=}CH{-}CH_2Cl$ | H | H | O | $CH_3$ | $CH_3$ | |
| $OCH_2CH{=}CHCH_2SCH_3$ | H | H | O | $OCH_3$ | $CH_3$ | |
| $OCH_2CH{=}CHCH_2SCH_3$ | H | H | O | $CH_3$ | $CH_3$ | |
| $OCH_2CH{=}CHS(O)CH_3$ | H | H | O | $OCH_3$ | $CH_3$ | |
| $OCH_2CH{=}CHS(O)CH_3$ | H | H | O | $CH_3$ | $CH_3$ | |
| $OCH_2CH{=}CHCH_2SO_2CH_3$ | H | H | O | $OCH_3$ | $CH_3$ | |
| $OCH_2CH{=}CHCH_2SO_2CH_3$ | H | H | O | $CH_3$ | $CH_3$ | |
| $OCH_2CH{=}CHCH_2OH$ | H | H | O | $OCH_3$ | $CH_3$ | |
| $OCH_2CH{=}CHCH_2OH$ | H | H | O | $CH_3$ | $CH_3$ | |
| $OCH{=}CH{-}CN$ | H | H | O | $OCH_3$ | $CH_3$ | |
| $OCH{=}CH{-}CN$ | H | H | O | $CH_3$ | $CH_3$ | |
| $OCH{=}CHCH_2NH_2$ | H | H | O | $OCH_3$ | $CH_3$ | |
| $OCH{=}CHCH_2NH_2$ | H | H | O | $CH_3$ | $CH_3$ | |
| $OCH_2CH{=}CHN(CH_3)_2$ | H | H | O | $OCH_3$ | $CH_3$ | |
| $OCH_2CH{=}CHN(CH_3)_2$ | H | H | O | $CH_3$ | $CH_3$ | |
| $OCH_2CH{=}CHC_6H_5$ | H | H | O | $OCH_3$ | $CH_3$ | |
| $OCH_2CH{=}CHC_6H_5$ | H | H | O | $CH_3$ | $CH_3$ | |
| $OCH_2C{\equiv}C{-}CH_3$ | H | H | O | $OCH_3$ | $CH_3$ | |
| $OCH_2C{\equiv}C{-}CH_3$ | H | H | O | $CH_3$ | $CH_3$ | |
| $OCH_2C{\equiv}CH$ | H | H | O | $OCH_3$ | $CH_3$ | |
| $OCH_2C{\equiv}CH$ | H | H | O | $CH_3$ | $CH_3$ | |
| $C{\equiv}CH$ | H | H | O | $OCH_3$ | $CH_3$ | |
| $C{\equiv}CH$ | H | H | O | $CH_3$ | $CH_3$ | |
| $C{\equiv}CCH_3$ | H | H | O | $OCH_3$ | $CH_3$ | |
| $C{\equiv}CCH_3$ | H | H | O | $CH_3$ | $CH_3$ | |
| $C{\equiv}CC_2H_5$ | H | H | O | $OCH_3$ | $CH_3$ | |
| $C{\equiv}CC_2H_5$ | H | H | O | $CH_3$ | $CH_3$ | |
| $C{\equiv}CCH_2Cl$ | H | H | O | $OCH_3$ | $CH_3$ | |
| $C{\equiv}CCH_2Cl$ | H | H | O | $CH_3$ | $CH_3$ | |
| $C{\equiv}CCHCl_2$ | H | H | O | $OCH_3$ | $CH_3$ | |
| $C{\equiv}CCHCl_2$ | H | H | O | $CH_3$ | $CH_3$ | |
| $C{\equiv}C{-}CH_2{-}CCl_3$ | H | H | O | $OCH_3$ | $CH_3$ | |
| $C{\equiv}C{-}CH_2{-}CCl_3$ | H | H | O | $CH_3$ | $CH_3$ | |
| $C{\equiv}CCH_2OH$ | H | H | O | $OCH_3$ | $CH_3$ | |
| $C{\equiv}CCH_2OH$ | H | H | O | $CH_3$ | $CH_3$ | |
| $C{\equiv}CCH_2OCH_3$ | H | H | O | $OCH_3$ | $CH_3$ | |
| $C{\equiv}CCH_2OCH_3$ | H | H | O | $CH_3$ | $CH_3$ | |
| $C{\equiv}CCH_2OC_2H_5$ | H | H | O | $OCH_3$ | $CH_3$ | |
| $C{\equiv}CCH_2OC_2H_5$ | H | H | O | $CH_3$ | $CH_3$ | |
| $C{\equiv}CCH_2SC_2H_5$ | H | H | O | $OCH_3$ | $CH_3$ | |
| $C{\equiv}CCH_2SC_2H_5$ | H | H | O | $CH_3$ | $CH_3$ | |
| $C{\equiv}CCH_2OCH_2CCl_3$ | H | H | O | $OCH_3$ | $CH_3$ | |
| $C{\equiv}CCH_2OCH_2CCl_3$ | H | H | O | $CH_3$ | $CH_3$ | |
| $C{\equiv}CCH_2CN$ | H | H | O | $OCH_3$ | $CH_3$ | |
| $C{\equiv}CCH_2CN$ | H | H | O | $CH_3$ | $CH_3$ | |
| $C{\equiv}CCH_2CO_2CH_3$ | H | H | O | $OCH_3$ | $CH_3$ | |
| $C{\equiv}CCH_2CO_2CH_3$ | H | H | O | $CH_3$ | $CH_3$ | |
| $C{\equiv}CCH(CH_3)CO_2C_2H_5$ | H | H | O | $OCH_3$ | $CH_3$ | |
| $C{\equiv}CCH(CH_3)CO_2C_2H_5$ | H | H | O | $CH_3$ | $CH_3$ | |
| $C{\equiv}CCH_2$—cyclopropyl | H | H | O | $OCH_3$ | $CH_3$ | |
| $C{\equiv}CCH_2$—cyclopropyl | H | H | O | $CH_3$ | $CH_3$ | |
| $C{\equiv}CCH_2C_6H_5$ | H | H | O | $OCH_3$ | $CH_3$ | |

TABLE III-continued

| | A = A-3 | | | | | |
|---|---|---|---|---|---|---|
| $R_1$ | $R_2$ | R | W | X | $Y_1$ | m.p. (°C.) |
| $C{=}CCH_2C_6H_5$ | H | H | O | $CH_3$ | $CH_3$ | |
| C=C—cyclopentyl | H | H | O | $OCH_3$ | $CH_3$ | |
| C=C—cyclopentyl | H | H | O | $CH_3$ | $CH_3$ | |
| C=C—cyclohexyl | H | H | O | $OCH_3$ | $CH_3$ | |
| C=C—cyclohexyl | H | H | O | $CH_3$ | $CH_3$ | |
| $C{=}CC_6H_5$ | H | H | O | $OCH_3$ | $CH_3$ | |
| $C{=}CC_6H_5$ | H | H | O | $CH_3$ | $CH_3$ | |
| $N_3$ | H | H | O | $OCH_3$ | $CH_3$ | |
| $N_3$ | H | H | O | $CH_3$ | $CH_3$ | |
| $P(O)(CH_3)OCH_3$ | H | H | O | $OCH_3$ | $CH_3$ | |
| $P(O)(CH_3)OCH_3$ | H | H | O | $CH_3$ | $CH_3$ | |
| $P(O)(OCH_3)_2$ | H | H | O | $OCH_3$ | $CH_3$ | |
| $P(O)(OCH_3)_2$ | H | H | O | $CH_3$ | $CH_3$ | |
| $P(O)(C_2H_5)OCH_3$ | H | H | O | $OCH_3$ | $CH_3$ | |
| $P(O)(C_2H_5)OCH_3$ | H | H | O | $CH_3$ | $CH_3$ | |
| $P(S)(CH_3)SCH_3$ | H | H | O | $OCH_3$ | $CH_3$ | |
| $P(S)(CH_3)SCH_3$ | H | H | O | $CH_3$ | $CH_3$ | |
| $P(S)(SCH_3)_2$ | H | H | O | $OCH_3$ | $CH_3$ | |
| $P(S)(SCH_3)_2$ | H | H | O | $CH_3$ | $CH_3$ | |
| $CH_2C(O)H$ | H | H | O | $OCH_3$ | $CH_3$ | |
| $CH_2C(O)H$ | H | H | O | $CH_3$ | $CH_3$ | |
| $CH_2C(O)CH_3$ | H | H | O | $OCH_3$ | $CH_3$ | |
| $CH_2C(O)CH_3$ | H | H | O | $CH_3$ | $CH_3$ | |
| $CH(Cl)CH_2CN$ | H | H | O | $OCH_3$ | $CH_3$ | |
| $CH(Cl)CH_2CN$ | H | H | O | $CH_3$ | $CH_3$ | |
| $CH(CH_3)CH_2NO_2$ | H | H | O | $OCH_3$ | $CH_3$ | |
| $CH(CH_3)CH_2NO_2$ | H | H | O | $CH_3$ | $CH_3$ | |
| $(CH_2)_2OCH_2CF_3$ | H | H | O | $OCH_3$ | $CH_3$ | |
| $(CH_2)_2OCH_2CF_3$ | H | H | O | $CH_3$ | $CH_3$ | |
| $(CH_2)_2OCH_2CCl_3$ | H | H | O | $OCH_3$ | $CH_3$ | |
| $(CH_2)_2OCH_2CCl_3$ | H | H | O | $CH_3$ | $CH_3$ | |
| $(CH_2)_2SCF_2H$ | H | H | O | $OCH_3$ | $CH_3$ | |
| $(CH_2)_2SCF_2H$ | H | H | O | $CH_3$ | $CH_3$ | |
| $(CH_2)_2SCF_2CF_2H$ | H | H | O | $OCH_3$ | $CH_3$ | |
| $(CH_2)_2SCF_2CF_2H$ | H | H | O | $CH_3$ | $CH_3$ | |
| $CCl{=}CCl_2$ | H | H | O | $OCH_3$ | $CH_3$ | |
| $CCl{=}CCl_2$ | H | H | O | $CH_3$ | $CH_3$ | |
| $CH{=}CHCH_2Cl$ | H | H | O | $OCH_3$ | $CH_3$ | |
| $CH{=}CHCH_2Cl$ | H | H | O | $CH_3$ | $CH_3$ | |
| $CH_2CH{=}CHCH_2Cl$ | H | H | O | $OCH_3$ | $CH_3$ | |
| $CH_2CH{=}CHCH_2Cl$ | H | H | O | $CH_3$ | $CH_3$ | |
| $CHCH{=}CBr_2$ | H | H | O | $OCH_3$ | $CH_3$ | |
| $CHCH{=}CBr_2$ | H | H | O | $CH_3$ | $CH_3$ | |
| $CHCH{=}CCH_2F$ | H | H | O | $OCH_3$ | $CH_3$ | |
| $CHCH{=}CCH_2F$ | H | H | O | $CH_3$ | $CH_3$ | |
| $CH{=}CHOCH_3$ | H | H | O | $OCH_3$ | $CH_3$ | |
| $CH{=}CHOCH_3$ | H | H | O | $CH_3$ | $CH_3$ | |
| $CH{=}CHCH_2OCH_3$ | H | H | O | $OCH_3$ | $CH_3$ | |
| $CH{=}CHCH_2OCH_3$ | H | H | O | $CH_3$ | $CH_3$ | |
| $CH{=}CHCN$ | H | H | O | $OCH_3$ | $CH_3$ | |
| $CH{=}CHCN$ | H | H | O | $CH_3$ | $CH_3$ | |
| $CH{=}CHCH_2OH$ | H | H | O | $OCH_3$ | $CH_3$ | |
| $CH{=}CHCH_2OH$ | H | H | O | $CH_3$ | $CH_3$ | |
| $CH{=}CHCH_2NO_2$ | H | H | O | $OCH_3$ | $CH_3$ | |
| $CH{=}CHCH_2NO_2$ | H | H | O | $CH_3$ | $CH_3$ | |
| $CH{=}CHCH_2SCH_3$ | H | H | O | $OCH_3$ | $CH_3$ | |
| $CH{=}CHCH_2SCH_3$ | H | H | O | $CH_3$ | $CH_3$ | |
| $CH_2CH{=}CHCH_2SO_2CH_3$ | H | H | O | $OCH_3$ | $CH_3$ | |
| $CH_2CH{=}CHCH_2SO_2CH_3$ | H | H | O | $CH_3$ | $CH_3$ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength | 90–99 | 0–10 | 0–2 |

-continued

| | Active Ingredient | Weight Percent* Diluent(s) | Surfactant(s) |
|---|---|---|---|
| Compositions | | | |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers". 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., N.Y., 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers on by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science". John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 9

Wettable Powder

| | |
|---|---|
| 2-(1,2-dichloroethenyloxy)-N—[(5,6-dihydro-4-methylfuro[2,3-d]pyrimidin-2-yl)aminocarbonyl]benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 10

Wettable Powder

| | |
|---|---|
| 2-(1,2-dichloroethenyloxy)-N—[(5,6-dihydro-4-methylfuro[2,3-d]pyrimidin-2-yl)aminocarbonyl]benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 11

Granule

| | |
|---|---|
| Wettable Powder of Example 10 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 12

Extruded Pellet

| | |
|---|---|
| 2-(difluoromethoxy)-N—[(5,6-dihydro-4-methylfuro-[2,3-d]pyrimidin-2-yl)aminocarbonyl]-6-methylbenzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 13

Oil Suspension

| | |
|---|---|
| 2-(1,2-dichloroethenyloxy)-N—[(5,6-dihydro-4-methyl-furo[2,3-d]pyrimidin-2-yl)aminocarbonyl]benzene-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 14

Wettable Powder

| | |
|---|---|
| 2-(difluoromethoxy)-N—[(5,6-dihydro-4-methylfuro-[2,3-d]pyrimidin-2-yl)aminocarbonyl]-6-methyl-benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 15

Low Strength Granule

| | |
|---|---|
| 2-(1,2-dichloroethenyloxy)-N—[(5,6-dihydro-4-methyl-furo[2,3-d]pyrimidin-2-yl)aminocarbonyl]benzene-sulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 16

Aqueous Suspension

| | |
|---|---|
| 2-(1,2-dichloroethenyloxy)-N—[(5,6-dihydro-4-methyl-furo[2,3-d]pyrimidin-2-yl)aminocarbonyl]benzene-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 17

Solution

| | |
|---|---|
| 2-(1,2-dichloroethenyloxy)-N—[(5,6-dihydro-4-methyl-furo[2,3-d]pyrimidin-2-yl)aminocarbonyl]benzene-sulfonamide | 5% |
| water | 95% |

The salt is added directly to the water with stirring to produce the solution, which may then be packaged for use.

EXAMPLE 18

Low Strength Granule

| | |
|---|---|
| 2-(1,2-dichloroethenyloxy)-N—[(5,6-dihydro-4-methyl-furo[2,3-d]pyrimidin-2-yl)aminocarbonyl]benzene-sulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 19

Granule

| | |
|---|---|
| 2-(1,2-dichloroethenyloxy)-N—[(5,6-dihydro-4-methyl-furo[2,3-d]pyrimidin-2-yl)aminocarbonyl]benzene-sulfonamide | 80% |
| wetting agent | 1% |
| crude ligninsulfonate salt (containing 5–20% of the natural sugars) | 10% |
| attapulgite clay | 9% |

The ingredients are blended and milled to pass throught a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less that 1%. The material is then discharged, screened to the desired size range, generally 14–100 mesh (1410–149 microns), and packaged for use.

EXAMPLE 20

High Strength Concentrate

| | |
|---|---|
| 2-(1,2-dichloroethenyloxy)-N—[(5,6-dihydro-4-methyl-furo[2,3-d]pyrimidin-2-yl)aminocarbonyl]benzene-sulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 21

Wettable Powder

| | |
|---|---|
| 2-(difluoromethoxy)-N—[(5,6-dihydro-4-methylfuro-[2,3-d]pyrimidin-2-yl)aminocarbonyl]-6-methyl-benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 22

Wettable Powder

| | |
|---|---|
| 2-(1,2-dichloroethenyloxy)-N—[(5,6-dihydro-4-methyl-furo[2,3-d]pyrimidin-2-yl)aminocarbonyl]benzene-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 23

Oil Suspension

| | |
|---|---|
| 2-(difluoromethoxy)-N—[(5,6-dihydro-4-methylfuro-[2,3-d]pyrimidin-2-yl)aminocarbonyl]-6-methyl-benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 24

Dust

| | |
|---|---|
| 2-(1,2-dichloroethenyloxy)-N—[(5,6-dihydro-4-methyl-furo[2,3-d]pyrimidin-2-yl)aminocarbonyl]benzene-sulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 25

Emulsifiable Concentrate

| | |
|---|---|
| 2-(1,2-dichloroethenyloxy)-N—[(5,6-dihydro-4-methyl-furo[2,3-d]pyrimidin-2-yl)aminocarbonyl]benzene-sulfonamide | 20% |
| | 20% |
| chlorobenzene | 74% |

-continued

| | |
|---|---|
| sorbitan monostearate and polyoxyethylene condensates thereof | 6% |

The ingredients are combined and stirred to produce a solution which can be emulsified in water for application.

Utility

Test results indicate that the compounds of the present invention are highly active preemergent of postemergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds may have utility for selective weed control in crops such as wheat. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, uracil, urea, amide, diphenylether, carbamate and bipyridylium types. The herbicidal properties of the subject compounds were discovered in a number of greenhouse tests. The test procedures and results follow.

Test A

Seeds of crabgrass (Digitaria spp.). barnyardgrass (*Echinochloa crusgalli*), wild oats (*Avena fatua*), cheatgrass (*Bromus secalinus*), sicklepod (*Cassia obtusifolia*), velvetleaf (*Abutilon theophrasti*), morningglory (Ipomoea spp.). cocklebur (*Xanthium pensylvanicum*), sorghum, corn, soybean, sugar beet, cotton, rice, wheat and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. A dash (—) response means no test. The accompanying descriptive symbols have the following meanings:

B=burn;
C=chlorosis or necrosis;
D=defoliation;
E=emergence inhibition;

G=growth retardation;
H=formative effects;
S=albinism;
U=unusual pigmentation;
X=axillary stimulation; and
6Y=abscised buds or flowers.

COMPOUNDS

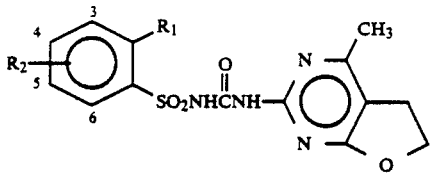

| Compound No. | $R_1$ | $R_2$ |
|---|---|---|
| 1 | $OCF_2H$ | 6-$CH_3$ |
| 2 | OC(Cl)=CHCl | H |
| 3 | $SCF_2H$ | H |

TABLE A

| Rate kg/ha | Cmpd. 1 0.05 | Cmpd. 2 0.05 | Cmpd. 3 0.4 |
|---|---|---|---|
| POSTEMERGENCE | | | |
| Morningglory | 10C | 5C,9G | 10C |
| Cocklebur | 9C | 6C,9G | 10C |
| Velvetleaf | — | 9C | — |
| Nutsedge | 9G | 7G | 4C,9G |
| Crabgrass | 5C,9G | 3G | 5C,9G |
| Barnyardgrass | 4C,9H | 3C,9H | 9C |
| Cheatgrass | — | 2C,8G | — |
| Wild Oats | 5C,9G | 4G | 5C,9G |
| Wheat | 3C,9G | 9G | 9C |
| Corn | 2C,9G | 5C,9G | 5U,9G |
| Soybean | 4C,9G | 5C,9G | 5C,9G |
| Rice | 9C | 6C,9G | 5C,9G |
| Sorghum | 4C,9G | 9H | 4U,9H |
| Sugar beet | 9C | 5C,9G | 9C |
| Cotton | 10C | 5C,9G | 10C |
| Sicklepod | 9C | — | 9C |
| PREEMERGENCE | | | |
| Morningglory | 9G | 8H | 9H |
| Cocklebur | — | — | 9H |
| Velvetleaf | — | 3C,8G | — |
| Nutsedge | 5C,9G | 9G | 9G |
| Crabgrass | 5C,9G | 3G | 9G |
| Barnyardgrass | 4C,9H | 3C,9H | 9H |
| Cheatgrass | — | 3C,9H | — |
| Wild Oats | 9C | 2C,7G | 5C,9G |
| Wheat | 9C | 2C,8G | 10E |
| Corn | 4C,9H | 2C,9G | 9H |
| Soybean | 9H | 2C,6G | 9H |
| Rice | 10E | 5G | 10E |
| Sorghum | 10H | 10E | 10E |
| Sugar beet | 5C,9G | 9G | 10E |
| Cotton | 9G | 9G | 9G |
| Sicklepod | 9G | — | 9G |

Test B

Postemergence

Two round pans (25 cm diameter by 12.5 cm deep) were filled with Sassafras sandy loam soil. One pan was planted with blackgrass (*Alopercurus myosuroides*). sugar beets, nutsedge (*Cyperus rotundus*) tubers, rape (*Brassica napus*), crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xantium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed postemergence with the chemicals dissolved in a non-phytotoxic solvent.

Preemergence

Two round pans (25 cm diameter by 12.5 cm deep) were filled with Sassafras sandy loam soil. One pan was planted with blackgrass, sugar beets, nutsedge, rape, crabgrass, sicklepod, teaweed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed preemergence with the chemicals dissolved in a non-phytotoxic solvent.

Treated plants and controls were maintained in the greenhouse for 28 days, then all treated plants were compared to controls and visually rated for plant response.

Response ratings are based on a scale of 0 to 100 where 0=no effect and 100=complete control.

Response ratings are contained in Table B.

TABLE B

| | Compound 1 | | | |
|---|---|---|---|---|
| Rate g/ha | 62 | 16 | 4 | 1 |
| POSTEMERGENCE | | | | |
| Corn | 100 | 100 | 100 | 80 |
| Wheat | 60 | 30 | 0 | 0 |
| Rice | 100 | 90 | 70 | 50 |
| Soybean | 100 | 100 | 100 | 80 |
| Cotton | 100 | 50 | 0 | 0 |
| Sugar beet | 100 | 100 | 60 | 20 |
| Rape | 100 | 100 | 80 | 50 |
| Crabgrass | 40 | 20 | 0 | 0 |
| Johnsongrass | 80 | 60 | 30 | 0 |
| Blackgrass | 100 | 80 | 50 | 20 |
| Barnyardgrass | 90 | 50 | 20 | 0 |
| Nutsedge | 70 | 50 | 0 | 0 |
| Giant Foxtail | 30 | 0 | 0 | 0 |
| Wild Oats | 60 | 70 | 30 | 0 |
| Cocklebur | 100 | 100 | 70 | 30 |
| Morningglory | 60 | 20 | 0 | 0 |
| Teaweed | 80 | 30 | 0 | 0 |
| Sicklepod | 40 | 0 | 0 | 0 |
| Jimsonweed | 30 | 0 | 0 | 0 |
| Velvetleaf | 100 | 100 | 70 | 20 |
| Rate g/ha | 250 | 62 | 16 | 4 |
| PREEMERGENCE | | | | |
| Corn | 100 | 80 | 60 | 0 |
| Wheat | 90 | 70 | 20 | 0 |
| Rice | 100 | 100 | 90 | 70 |
| Soybean | 100 | 80 | 30 | 0 |
| Cotton | 70 | 0 | 0 | 0 |
| Sugar beet | 90 | 90 | 50 | 0 |
| Rape | 100 | 90 | 50 | 0 |
| Crabgrass | 90 | 90 | 70 | 20 |
| Johnsongrass | 100 | 90 | 80 | 30 |
| Blackgrass | 100 | 100 | 90 | 70 |
| Barnyardgrass | 100 | 90 | 70 | 20 |
| Nutsedge | 90 | 80 | 70 | 20 |
| Giant Foxtail | 100 | 90 | 60 | 0 |
| Wild Oats | 100 | 90 | 70 | 60 |
| Cocklebur | 90 | 70 | 40 | 0 |
| Morningglory | 30 | 20 | 0 | 0 |
| Teaweed | 90 | 90 | 40 | 0 |
| Sicklepod | 90 | 80 | 50 | 20 |
| Jimsonweed | 90 | 70 | 30 | 0 |
| Velvetleaf | 100 | 90 | 70 | 20 |
| | Compound 2 | | | |
| Rate g/ha | 62 | 16 | 4 | |
| POSTEMERGENCE | | | | |

TABLE B-continued

| | | | | |
|---|---|---|---|---|
| Corn | 100 | 100 | 60 | |
| Wheat | 80 | 50 | 0 | |
| Rice | 100 | 90 | 30 | |
| Soybean | 90 | 90 | 60 | |
| Cotton | 90 | 30 | 0 | |
| Sugar beet | 70 | 60 | 30 | |
| Rape | 100 | 80 | 30 | |
| Crabgrass | 50 | 20 | 0 | |
| Johnsongrass | 90 | 30 | 0 | |
| Blackgrass | 100 | 90 | 40 | |
| Barnyardgrass | 40 | 20 | 0 | |
| Nutsedge | 80 | 20 | 0 | |
| Giant Foxtail | 30 | 0 | 0 | |
| Wild Oats | 20 | 0 | 0 | |
| Cocklebur | 100 | 90 | 60 | |
| Morningglory | 70 | 30 | 20 | |
| Teaweed | 40 | 0 | 0 | |
| Sicklepod | 30 | 0 | 0 | |
| Jimsonweed | 50 | 0 | 0 | |
| Velvetleaf | 90 | 70 | 20 | |
| Rate g/ha | 250 | 62 | 16 | 4 |
| PREEMERGENCE | | | | |
| Corn | 90 | 80 | 20 | 0 |
| Wheat | 90 | 60 | 20 | 0 |
| Rice | 90 | 80 | 40 | 0 |
| Soybean | 70 | 20 | 0 | 0 |
| Cotton | 30 | 0 | 0 | 0 |
| Sugar beet | 90 | 60 | 40 | 20 |
| Rape | 90 | 20 | 0 | 0 |
| Crabgrass | 70 | 20 | 0 | 0 |
| Johnsongrass | 100 | 100 | 90 | 50 |
| Blackgrass | 90 | 90 | 90 | 70 |
| Barnyardgrass | 80 | 60 | 30 | 0 |
| Nutsedge | — | — | — | 20 |
| Giant Foxtail | 70 | 60 | 20 | 0 |
| Wild Oats | 60 | 40 | 20 | 0 |
| Cocklebur | 90 | 60 | 50 | 20 |
| Morningglory | 20 | 0 | 0 | 0 |
| Teaweed | 80 | 70 | 50 | 20 |
| Sicklepod | 60 | 0 | 0 | 0 |
| Jimsonweed | 90 | 80 | 50 | 20 |
| Velvetleaf | 70 | 30 | 20 | 0 |

What is claimed is:

1. A compound of the formula

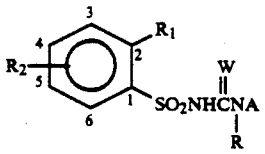

I wherein

W is O or S;

R is H or $CH_3$;

A is

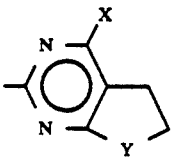

A-1

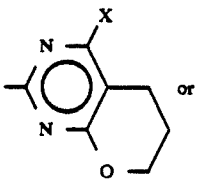

A-2

-continued

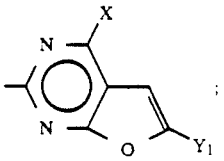

A-3

X is H, $CH_3$, $C_2H_5$, $OCH_3$, $OC_2H_5$, Cl, $OCF_2H$, $SCH_3$ or $N(CH_3)_2$;

Y is O or $CH_2$;

$Y_1$ is H, $CH_3$ or $C_2H_5$;

$R_1$ is $QR_3$, —C≡$CR_4$, $N_3$, $P(W_1)R_5R_6$, —$CR_7R_8R_9$ or $C_2$–$C_4$ alkenyl substituted with CN, OH, $NO_2$ or $S(O)_nR_{10}$;

$R_2$ is H, F, Cl, Br, $CF_3$, CN, $NO_2$, $C_1$–$C_2$ alkyl, $C_1$–$C_2$ alkoxy, $C_1$–$C_2$ alkylthio, $C_1$–$C_2$ haloalkyl, $C_1$–$C_2$ haloalkoxy, $C_1$–$C_2$ haloalkylthio, $C_1$–$C_2$ alkylsulfinyl, $C_1$–$C_2$ alkylsulfonyl, $CH_2OCH_3$, $CH_2SCH_3$, $C_3$ alkenyloxy or $C_3$ alkynyloxy;

Q is O, S, SO or $SO_2$;

$R_3$ is $C_1$–$C_4$ alkyl substituted with $C_1$–$C_2$ alkoxy, $C_1$–$C_2$ alkylthio, $C_1$–$C_2$ alkylsulfinyl, $C_1$–$C_2$ alkylsulfonyl, $C_1$–$C_2$ haloalkoxy, $C_1$–$C_2$ haloalkylthio, $C_1$–$C_2$ haloalkylsulfinyl, $C_1$–$C_2$ haloalkylsulfonyl, OH, CN, $NH_2$, $C_1$–$C_2$ alkylamino, di($C_1$–$C_2$)alkylamino or phenyl; or $R_3$ is $C_2$–$C_4$ alkenyl [optionally] substituted with the substituents mentioned above; or $R_3$ is $C_2$–$C_4$ alkynyl;

$R_4$ is H or $C_1$–$C_2$ alkyl optionally substituted with halogen, OH, $C_1$–$C_2$ alkoxy, $C_1$–$C_2$ alkylthio, $C_1$–$C_2$ haloalkoxy, CN, $C_2$–$C_3$ alkoxycarbonyl, cyclopropyl or phenyl; or $R_4$ is $C_3$–$C_6$ cycloalkyl or phenyl;

$W_1$ is O or S;

$R_5$ and $R_6$ are independently $C_1$–$C_2$ alkyl, $C_1$–$C_2$ alkoxy or $C_1$–$C_2$ alkylthio;

$R_7$ is H, $CH_3$ or halogen;

$R_8$ is H or $CH_3$;

$R_9$ is $C(O)R_{11}$ or $C_1$–$C_2$ alkyl substituted with one or more groups selected from $C(O)R_{11}$, CN, $NO_2$, $C_1$–$C_2$ haloalkoxy or $C_1$–$C_2$ haloalkylthio;

$R_{10}$ is $C_1$–$C_2$ alkyl;

$R_{11}$ is H or $C_1$–$C_2$ alkyl; and n is 0, 1 or 2;

and their agriculturally suitable salts; provided that when $R_3$ is substituted with OH or $NH_2$, said substituents must be separated from Q by at least two carbon atoms.

2. Compounds of claim 1 where W is O and R is H.

3. Compounds of claim 2 where $R_1$ is $OR_3$, $SR_3$, $SO_2R_3$, —C $CR_4$, $N_3$, $P(O)R_5R_6$, —$CH_2R_9$ or $C_2$–$C_4$ alkenyl substituted with CN, OH, $NO_2$, $SCH_3$, $SC_2H_5$, $SO_2CH_3$, $SO_2C_2H_5$;

$R_2$ is H, Cl, Br, F, $CH_3$, $C_2H_5$, $OCH_3$, $OC_2H_5$, $SCH_3$, CN, $CF_3$, $OCF_2H$, $SCF_2H$, $CH_2OCH_3$ or $CH_2SCH_3$, and $R_2$ must be H when in the 4 position;

$R_3$ is $C_1$–$C_3$ alkyl substituted with F, Cl, Br, $OCH_3$, $OC_2H_5$, $SCH_3$, $SC_2H_5$, $SO_2CH_3$, $SO_2C_2H_5$, $OCF_2H$, $OCH_2CF_3$, $SCF_2H$, $SO_2CF_3$, OH, CN, $NH_2$, $NHCH_3$, $N(CH_3)_2$ or phenyl; or $R_3$ is $C_3$–$C_4$ alkynyl;

$R_4$ is H or $C_1$–$C_2$ alkyl optionally substituted with halogen, OH, CN, $OCH_3$, $SCH_3$, $OCF_2H$, $OCH_2CF_3$, cyclopropyl, $CO_2CH_3$ or phenyl;

$R_5$ and $R_6$ are independently $C_1$–$C_2$ alkyl or $C_1$–$C_2$ alkoxy; and $R_9$ is $C(O)CH_3$, $CH_2CH_2CN$, $CH_2CN$, $CH_2C(O)CH_3$, $CH_2CH_2C(O)CH_3$, $CH_2OCF_2H$ or $CH_2SCF_2H$.

4. Compounds of claim 3 where X is $CH_3$, $OCH_3$, $OC_2H_5$ or $OCF_2H$; and $Y_1$ is H or $CH_3$.

5. Compounds of claim 4 where $R_1$ is $OR_3$, $SR_3$, $SO_2R_3$, —C≡CH, —C≡$CCH_3$, $N_3$, $P(O)(OCH_3)_2$, $P(O)(CH_3)_2$;

$R_2$ is H, Cl, $CH_3$ or $OCH_3$; and $R_3$ is $C_1$–$C_2$ alkyl substituted with F, Cl, Br, $OCH_3$ or $OC_2H_5$.

6. Compounds of claim 5 where A is A-1.

7. Compounds of claim 5 where A is A-2.

8. Compounds of claim 5 where A is A-3.

9. A composition suitable for controlling the growth of undesired vegetation which comprises an effective amount of a compound of claim 1 and at least one of the following: surfactant, solid or liquid diluent.

10. A composition suitable for controlling the growth of undesired vegetation which comprises an effective amount of a compound of claim 2 and at least one of the following: surfactant, solid or liquid diluent.

11. A composition suitable for controlling the growth of undesired vegetation which comprises an effective amount of a compound of claim 3 and at least one of the following: surfactant, solid or liquid diluent.

12. A composition suitable for controlling the growth of undesired vegetation which comprises an effective amount of a compound of claim 4 and at least one of the following: surfactant, solid or liquid diluent.

13. A composition suitable for controlling the growth of undesired vegetation which comprises an effective amount of a compound of claim 5 and at least one of the following: surfactant, solid or liquid diluent.

14. A composition suitable for controlling the growth of undesired vegetation which comprises an effective amount of a compound of claim 6 and at least one of the following: surfactant, solid or liquid diluent.

15. A composition suitable for controlling the growth of undesired vegetation which comprises an effective amount of a compound of claim 7 and at least one of the following: surfactant, solid or liquid diluent.

16. A composition suitable for controlling the growth of undesired vegetation which comprises an effective amount of a compound of claim 8 and at least one of the following: surfactant, solid or liquid diluent.

17. A method for controlling the growth of undesired vegetation which comprises applying to the locus to be protected an effective amount of a compound of claim 1.

18. A method for controlling the growth of undesired vegetation which comprises applying to the locus to be protected an effective amount of a compound of claim 2.

19. A method for controlling the growth of undesired vegetation which comprises applying to the locus to be protected an effective amount of a compound of claim 3.

20. A method for controlling the growth of undesired vegetation which comprises applying to the locus to be protected an effective amount of a compound of claim 4.

21. A method for controlling the growth of undesired vegetation which comprises applying to the locus to be protected an effective amount of a compound of claim 5.

22. A method for controlling the growth of undesired vegetation which comprises applying to the locus to be protected an effective amount of a compound of claim 6.

23. A method for controlling the growth of undesired vegetation which comprises applying to the locus to be protected an effective amount of a compound of claim 7.

24. A method for controlling the growth of undesired vegetation which comprises applying to the locus to be protected an effective amount of a compound of claim 8.

* * * * *